(12) United States Patent
Baker-Glenn et al.

(10) Patent No.: US 9,145,402 B2
(45) Date of Patent: Sep. 29, 2015

(54) AMINOPYRIMIDINE DERIVATIVES AS LRRK2 MODULATORS

(71) Applicant: Genentech, Inc., South San Francisco, CA (US)

(72) Inventors: Charles Baker-Glenn, St. Neots (GB); Mark Chambers, Puckeridge (GB); Bryan K. Chan, San Carlos, CA (US); Anthony Estrada, San Carlos, CA (US); Daniel Shore, San Francisco, CA (US); Zachary Kevin Sweeney, Redwood City, CA (US); Huifen Chen, Burlingame, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/687,411

(22) Filed: Nov. 28, 2012

(65) Prior Publication Data

US 2013/0158032 A1    Jun. 20, 2013

Related U.S. Application Data

(60) Provisional application No. 61/564,753, filed on Nov. 29, 2011.

(51) Int. Cl.
| | | |
|---|---|---|
| *A61K 31/535* | (2006.01) | |
| *A61K 31/505* | (2006.01) | |
| *C07D 413/10* | (2006.01) | |
| *C07D 413/12* | (2006.01) | |
| *C07D 239/02* | (2006.01) | |
| *C07D 239/48* | (2006.01) | |
| *C07D 401/12* | (2006.01) | |
| *C07D 403/12* | (2006.01) | |
| *C07D 239/42* | (2006.01) | |
| *C07D 405/12* | (2006.01) | |
| *C07D 401/04* | (2006.01) | |
| *C07D 403/04* | (2006.01) | |

(52) U.S. Cl.
CPC ............ *C07D 413/12* (2013.01); *C07D 239/42* (2013.01); *C07D 239/48* (2013.01); *C07D 401/04* (2013.01); *C07D 401/12* (2013.01); *C07D 403/04* (2013.01); *C07D 403/12* (2013.01); *C07D 405/12* (2013.01)

(58) Field of Classification Search
CPC . A61K 31/535; A61K 31/505; C07D 413/10; C07D 413/12; C07D 239/02; C07D 239/48; C07D 401/12; C07D 403/12
USPC .................. 514/235.8, 275; 544/323, 122
See application file for complete search history.

(56) References Cited

U.S. PATENT DOCUMENTS

| | | |
|---|---|---|
| 8,354,420 B2 | 1/2013 | Baker-Glenn et al. |
| 2010/0081679 A1* | 4/2010 | Greul et al. ............. 514/275 |
| 2012/0157427 A1 | 6/2012 | Baker-Glenn et al. |

OTHER PUBLICATIONS

Michael Kothe et al., Selectivity-determining Residues in Plk1, Chem. Biol. Drug Des. 2007, 70: pp. 540-546.*

* cited by examiner

*Primary Examiner* — James O Wilson
*Assistant Examiner* — Ebenezer O Sackey
(74) *Attorney, Agent, or Firm* — Robert C. Hall

(57) ABSTRACT

Compounds of the formula I:

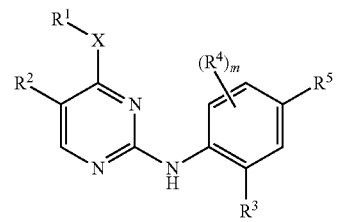

or pharmaceutically acceptable salts thereof,
wherein m, n, X, $R^1$, $R^2$, $R^3$, $R^4$ and $R^5$ are as defined herein. Also disclosed are methods of making the compounds and using the compounds for treatment of diseases associated with LRRK2 receptor, such as Parkinson's disease.

20 Claims, No Drawings

AMINOPYRIMIDINE DERIVATIVES AS LRRK2 MODULATORS

CROSS REFERENCE TO RELATED APPLICATION

This Application claims the benefit under 35 USC §119 of U.S. Provisional Application Ser. No. 61/564,753 filed on Nov. 29, 2011, the disclosure of which is incorporated herein by reference.

FIELD OF THE INVENTION

This invention pertains to compounds that modulate the function of LRRK2 and are useful for treatment of LRRK2-mediated diseases and conditions such as Parkinson's disease.

BACKGROUND OF THE INVENTION

Neurodegenerative diseases such as Parkinson's disease, Lewy body dementia and Huntington's disease affect millions of individuals. Parkinson's disease is a chronic, progressive motor system disorder that afflicts approximately one out of every 1000 people, with hereditary Parkinson's disease accounting for 5-10% of all of patients. Parkinson's disease is caused by progressive loss of mid-brain dopamine neurons, leaving patients with impaired ability to direct and control their movements. The primary Parkinson's disease symptoms are trembling, rigidity, slowness of movement, and impaired balance. Many Parkinson's disease patients also experience other symptoms such as emotional changes, memory loss, speech problems, and sleeping disorders.

The gene encoding the leucine-rich repeat kinase 2 protein (LRRK2) has been identified in association with hereditary Parkinson's disease (Paisan-Ruiz et al., *Neuron*, Vol. 44(4), 2004, pp 595-600; Zimprich et al., *Neuron*, Vol. 44(4), 2004, 601-607). In-vitro studies show that Parkinson's disease-associated mutation leads to increased LRRK2 kinase activity and decreased rate of GTP hydrolysis compared to wild-type (Guo et al., *Experimental Cell Research*, Vol. 313(16), 2007, pp. 3658-3670. Anti-LRRK2 antibodies have been used to label brainstem Lewy bodies associated with Parkinson's disease and cortical antibodies associated with Lewis body dementia suggesting that LRRK2 may play an important role in Lewie body formation and pathogenesis associated with these diseases (Zhou et al., *Molecular Degeneration*, 2006, 1:17 doi:10.1186/1750-1326-1-17). LRRK2 has also been identified as a gene potentially associated with increased susceptibility to Crohn's disease and susceptibility to leprosy (Zhang et al., *New England J. Med.* Vol. 361 (2009) pp. 2609-2618.

LRRK2 has also been associated with the transition of mild cognitive impairment to Alzheimer's disease (WO2007/149789); L-Dopa induced dyskinesia (Hurley et al., *Eur. J. Neurosci.*, Vol. 26, 2007, pp. 171-177; CNS disorders associated with neuronal progenitor differentiation (Milosevic et al., *Neurodegen.*, Vol. 4, 2009, p. 25); cancers such as kidney, breast, prostate, blood and lung cancers and acute myelogenous leukemia (WO2011/038572); papillary renal and thyroid carcinomas (Looyenga et al., www.pnas.org/cgi/doi/10.1073/pnas.1012500108); multiple myeloma (Chapman et al., *Nature* Vol. 471, 2011, pp. 467-472); amyotrophic lateral sclerosis (Shtilbans et al., *Amyotrophic Lateral Sclerosis* "Early Online 2011, pp. 1-7); rheumatoid arthritis (Nakamura et al., *DNA Res*. Vol. 13(4), 2006, pp. 169-183); and ankylosing spondylytis (Danoy et al., *PLoS Genetics*, Vol. 6(12), 2010, e1001195, pp. 1-5).

Accordingly, compounds and compositions effective at modulating LRRK2 activity may provide a treatment for neurodegenerative diseases such as Parkinson's disease and Lewie body dementia, for CNS disorders such as Alzheimer's disease and L-Dopa induced dyskinesia, for cancers such as kidney, breast, prostate, blood, papillary and lung cancers, acute myelogenous leukemia and multiple myeloma, and for inflammatory diseases such as leprosy, Crohn's disease, amyotrophic lateral sclerosis, rheumatoid arthritis, and ankylosing spondylytis. Particularly, there is a need for compounds with LRRK2 affinity that are selective for LRRK2 over other kinases, such as JAK2, and which can provide effective drugs for treatment of neurodegenerative disorders such as Parkinson's disease.

SUMMARY OF THE INVENTION

The invention provides compounds of the formula I:

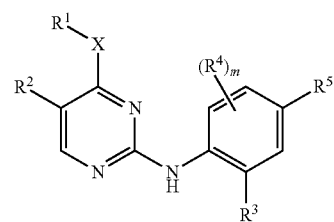

or pharmaceutically acceptable salts thereof,
wherein:
  m is from 0 to 3;
  X is: —$NR^a$—; —O—; or —$S(O)_r$— wherein r is from 0 to 2 and $R^a$ is hydrogen or $C_{1-6}$alkyl;
  $R^1$ is: $C_{1-6}$alkyl; $C_{1-6}$alkenyl; $C_{1-6}$alkynyl; halo-$C_{1-6}$alkyl; $C_{1-6}$alkoxy-$C_{1-6}$alkyl; hydroxy-$C_{1-6}$alkyl; amino-$C_{1-6}$alkyl; $C_{1-6}$alkylsulfonyl-$C_{1-6}$alkyl; $C_{3-6}$cycloalkyl optionally substituted with $C_{1-6}$alkyl; $C_{3-6}$cycloalkyl-$C_{1-6}$alkyl wherein the $C_{3-6}$cycloalkyl portion is optionally substituted with $C_{1-6}$alkyl; tetrahydrofuranyl; tetrahydrofuranyl-$C_{1-6}$ alkyl; oxetanyl; or oxetan-$C_{1-6}$ alkyl;
  or $R^1$ and $R^a$ together with the atoms to which they are attached may form a three to six membered ring that may optionally include an additional heteroatom selected from O, N and S, and which is substituted with oxo, halo or $C_{1-6}$alkyl;
  $R^2$ is: halo; $C_{1-6}$alkoxy; cyano; $C_{1-6}$alkynyl; $C_{1-6}$alkenyl; halo-$C_{1-6}$alkyl; halo-$C_{1-6}$alkoxy; $C_{3-6}$cycloalkyl wherein the $C_{3-6}$cycloalkyl portion is optionally substituted with $C_{1-6}$alkyl; $C_{3-6}$cycloalkyl-$C_{1-6}$alkyl wherein the $C_{3-6}$cycloalkyl portion is optionally substituted with $C_{1-6}$alkyl; tetrahydrofuranyl; tetrahydrofuranyl-$C_{1-6}$alkyl; acetyl; oxetanyl; or oxetan-$C_{1-6}$ alkyl;
  $R^3$ and $R^4$ each independently is: halo; $C_{1-6}$alkyl; $C_{1-6}$alkoxy; $C_{3-6}$cycloalkyloxy; halo-$C_{1-6}$alkyl; or halo-$C_{1-6}$alkoxy;
  or $R^3$ and $R^4$ together with the atoms to which they are attached may form a five-or six-membered ring that optionally includes one or two heteroatoms each independently selected from O, N and S, the ring being optionally substituted one or more times with $R^6$;
  $R^5$ is: $C_{1-6}$alkyl-sulfonyl; $C_{3-6}$cycloalkylsulfonyl; $C_{3-6}$cycloalkyl-$C_{1-6}$ alkylsulfonyl; cyano; cyano-$C_{1-6}$alkyl; heterocyclyl optionally substituted one or more times with $R^6$; heterocyclyl-$C_{1-6}$alkyl wherein the heterocyclyl moiety is optionally substituted one or more times with $R^6$; halo-$C_{1-6}$ alkyl; heterocyclyl-sulfonyl wherein the heterocyclyl moiety is optionally substituted one or more times with $R^6$; or carboxy; and $R^6$ is: $C_{1-6}$ alkyl; halo; halo-$C_{1-6}$ alkyl; or oxo.

The invention also provides and pharmaceutical compositions comprising the compounds, methods of using the compounds, and methods of preparing the compounds.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" and "alkyloxy", which may be used interchangeably, mean a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^a$—O—$R^b$—, where $R^a$ is alkyl and $R^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkoxyalkoxy' means a group of the formula —O—R—R' wherein R is alkylene and R' is alkoxy as defined herein.

"Alkylcarbonyl" means a moiety of the formula —C(O)—R, wherein R is alkyl as defined herein.

"Alkoxycarbonyl" means a group of the formula —C(O)—R wherein R is alkoxy as defined herein.

"Alkylcarbonylalkyl" means a group of the formula —R—C(O)—R wherein R is alkylene and R' is alkyl as defined herein.

"Alkoxycarbonylalkyl" means a group of the formula —R—C(O)—R wherein R is alkylene and R' is alkoxy as defined herein.

"Alkoxycarbonylalkoxy"means a group of the formula —O—R—C(O)—R' wherein R is alkylene and R' is alkoxy as defined herein.

"Hydroxycarbonylalkoxy" means a group of the formula —O—R—C(O)—OH wherein R is alkylene as defined herein.

"Alkylaminocarbonylalkoxy" means a group of the formula —O—R—C(O)—NHR' wherein R is alkylene and R' is alkyl as defined herein.

"Dialkylaminocarbonylalkoxy" means a group of the formula —O—R—C(O)—NR'R" wherein R is alkylene and R' and R" are alkyl as defined herein.

"Alkylaminoalkoxy" means a group of the formula —O—R—NHR' wherein R is alkylene and R' is alkyl as defined herein.

"Dialkylaminoalkoxy" means a group of the formula —O—R—NR'R' wherein R is alkylene and R' and R" are alkyl as defined herein.

"Alkylsulfonyl" means a moiety of the formula —$SO_2$—R, wherein R is alkyl as defined herein.

"Alkylsulfonylalkyl means a moiety of the formula —R'—$SO_2$—R" where where R' is alkylene and R" is alkyl as defined herein.

"Alkylsulfonylalkoxy" means a group of the formula —O—R—$SO_2$—R' wherein R is alkylene and R' is alkyl as defined herein.

"Amino means a moiety of the formula —NRR' wherein R and R' each independently is hyrdogen or alkyl as defined herein. "Amino thus includes "alkylamino (where one of R and R' is alkyl and the other is hydrogen) and "dialkylamino (where R and R' are both alkyl.

"Aminocarbonyl" means a group of the formula —C(O)—R wherein R is amino as defined herein.

"Alkoxyamino" means a moiety of the formula —NR—OR' wherein R is hydrogen or alkyl and R' is alkyl as defined herein.

"Alkylsulfanyl" means a moiety of the formula —SR wherein R is alkyl as defined herein.

"Aminoalkyl" means a group —R—R' wherein R' is amino and R is alkylene as defined herein. "Aminoalkyl" includes aminomethyl, aminoethyl, 1-aminopropyl, 2-aminopropyl, and the like. The amino moiety of "aminoalkyl" may be substituted once or twice with alkyl to provide "alkylaminoalkyl" and "dialkylaminoalkyl" respectively. "Alkylaminoalkyl" includes methylaminomethyl, methylaminoethyl, methylaminopropyl, ethylaminoethyl and the like. "Dialkylaminoalkyl" includes dimethylaminomethyl, dimethylaminoethyl, dimethylaminopropyl, N-methyl-N-ethylaminoethyl, and the like.

"Aminoalkoxy" means a group —OR—R' wherein R' is amino and R is alkylene as defined herein.

"Alkylsulfonylamido" means a moiety of the formula —NR'$SO_2$—R wherein R is alkyl and R' is hydrogen or alkyl.

"Aminocarbonyloxyalkyl" or "carbamylalkyl" means a group of the formula —R—O—C(O)—NR'R" wherein R is alkylene and R', R" each independently is hydrogen or alkyl as defined herein.

"Alkynylalkoxy" means a group of the formula —O—R—R' wherein R is alkylene and R' is alkynyl as defined herein.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, of which may be optionally substituted as defined herein.

"Arylalkyl" and "Aralkyl", which may be used interchangeably, mean a radical-$R^aR^b$ where $R^a$ is an alkylene group and $R^b$ is an aryl group as defined herein; e.g., phenylalkyls such as benzyl, phenylethyl, 3-(3-chlorophenyl)-2-methylpentyl, and the like are examples of arylalkyl.

"Arylsulfonyl means a group of the formula —$SO_2$—R wherein R is aryl as defined herein.

"Aryloxy" means a group of the formula —O—R wherein R is aryl as defined herein.

"Aralkyloxy" means a group of the formula —O—R—R" wherein R is alkylene and R' is aryl as defined herein.

"Carboxy" or "hydroxycarbonyl", which may be used interchangeably, means a group of the formula —C(O)—OH.

"Cyanoalkyl" means a moiety of the formula —R'—R", where R' is alkylene as defined herein and R" is cyano or nitrile.

"Cycloalkyl" means a monovalent saturated carbocyclic moiety consisting of mono- or bicyclic rings. Particular cycloalkyl are unsubstituted or substituted with alkyl. Cycloalkyl can optionally be substituted as defined herein. Unless defined otherwise, cycloalkyl may be optionally substitued with one or more substituents, wherein each substituent is independently hydroxy, alkyl, alkoxy, halo, haloalkyl, amino, monoalkylamino, or dialkylamino. Examples of cycloalkyl moieties include, but are not limited to, cyclopropyl, cyclobutyl, cyclopentyl, cyclohexyl, cycloheptyl, and the like, including partially unsaturated (cycloalkenyl) derivatives thereof.

"Cycloalkylalkyl" means a moiety of the formula —R'—R", where R' is alkylene and R" is cycloalkyl as defined herein.

"Cycloalkylalkoxy" means a group of the formula —O—R—R' wherein R is alkylene and R' is cycloalkyl as defined herein.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, each of which may be optionally substituted as defined herein.

Heteroarylalkyl" or "heteroaralkyl" means a group of the formula —R—R' wherein R is alkylene and R' is heteroaryl as defined herein.

"Heteroarylsulfonyl means a group of the formula —$SO_2$—R wherein R is heteroaryl as defined herein.

"Heteroaryloxy" means a group of the formula —O—R wherein R is heteroaryl as defined herein.

"Heteroaralkyloxy" means a group of the formula —O—R—R" wherein R is alkylene and R' is heteroaryl as defined herein.

The terms "halo", "halogen" and "halide", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —$CH_2Cl$, —$CH_2CF_3$, —$CH_2CCl_3$, perfluoroalkyl (e.g., —$CF_3$), and the like.

"Haloalkoxy" means a moiety of the formula —OR, wherein R is a haloalkyl moiety as defined herein. An exemplary haloalkoxy is difluoromethoxy.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, morpholinyl, thiomorpholinyl, azepinyl, pyrrolidinyl, azetidinyl, tetrahydropyranyl, tetrahydrofuranyl, oxetanyl and the like. Such heterocyclyl may be optionally substituted as defined herein.

"Heterocyclylalkyl" means a moiety of the formula —R—R' wherein R is alkylene and R' is heterocyclyl as defined herein.

"Heterocyclyloxy" means a moiety of the formula —OR wherein R is heterocyclyl as defined herein.

"Heterocyclylalkoxy" means a moiety of the formula —OR—R' wherein R is alkylene and R' is heterocyclyl as defined herein.

"Heterocyclylsulfonyl" means a group of formula —$SO_2$—R wherein R is heterocyclyl as defined herein.

"Hydroxyalkoxy" means a moiety of the formula —OR wherein R is hydroxyalkyl as defined herein.

"Hydroxyalkylamino" means a moiety of the formula —NR—R' wherein R is hydrogen or alkyl and R' is hydroxyalkyl as defined herein.

"Hydroxyalkylaminoalkyl" means a moiety of the formula —R—NR'—R" wherein R is alkylene, R' is hydrogen or alkyl, and R" is hydroxyalkyl as defined herein.

"Hydroxycarbonylalkyl" or "carboxyalkyl" means a group of the formula —R—(CO)—OH where R is alkylene as defined herein.

"Hydroxycarbonylalkoxy" means a group of the formula —O—R—C(O)—OH wherein R is alkylene as defined herein.

"Hydroxyalkyloxycarbonylalkyl" or "hydroxyalkoxycarbonylalkyl" means a group of the formula —R—C(O)—O—R—OH wherein each R is alkylene and may be the same or different.

"Hydroxyalkyl" means an alkyl moiety as defined herein, substituted with one or more, for example, one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Hydroxycycloalkyl" means a cycloalkyl moiety as defined herein wherein one, two or three hydrogen atoms in the cycloalkyl radical have been replaced with a hydroxy substituent. Representative examples include, but are not limited to, 2-, 3-, or 4-hydroxycyclohexyl, and the like.

"Alkoxy hydroxyalkyl" and "hydroxy alkoxyalkyl", which may be used interchangeably, means an alkyl as defined herein that is substituted at least once with hydroxy and at least once with alkoxy. "Alkoxy hydroxyalkyl" and "hydroxy alkoxyalkyl" thus encompass, for example, 2-hydroxy-3-methoxy-propan-1-yl and the like.

"Urea" or "ureido" means a group of the formula —NR'—C(O)—NR"R'" wherein R', R" and R'" each independently is hydrogen or alkyl.

"Carbamate" means a group of the formula —O—C(O)—NR'R" wherein R' and R" each independently is hydrogen or alkyl.

"Carboxy" means a group of the formula —O—C(O)—OH.

"Sulfonamido" means a group of the formula —SO$_2$—NR'R" wherein R', R" and R'" each independently is hydrogen or alkyl.

"Optionally substituted" when used in association with an "aryl", phenyl", "heteroaryl" "cycloalkyl" or "heterocyclyl" moiety means that such moiety may be unsubstituted (i.e., all open valencies are occupied by a hydrogen atom) or substituted with specific groups as related herein.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound.

It should be understood that all references to pharmaceutically acceptable salts include solvent addition forms (solvates) or crystal forms (polymorphs) as defined herein, of the same acid addition salt.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The artisan in the art will know how to chose a group for the ease of removal and for the ability to withstand the following reactions.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as H$_2$O, such combination being able to form one or more hydrate.

"Parkinson's disease" means a degenerative disorder of the central nervous system that impairs motor skills, speech, and/or cognitive function. Symptoms of Parkinson's disease may include, for example, muscle rigidity, tremor, slowing of physical movement (bradykinesia) and loss of physical movement (akinesia).

"Lewie body disease" also called "Lewie body demntia", diffuse Lewy body disease", cortical Lewie body disease", means a neurogenerative disorder characterized anatomically by the presence of Lewie bodies in the brain.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as particular definitions, if any.

"Treating" or "treatment" of a disease state includes, inter alia, inhibiting the disease state, i.e., arresting the development of the disease state or its clinical symptoms, and/or relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature and chemical names used in this Application are based on ChembioOffice™ by CambridgeSoft™. Any open valency appearing on a carbon, oxygen sulfur or nitrogen atom in the structures herein indicates the presence of a hydrogen atom unless indicated otherwise. Where a nitrogen-containing heteroaryl ring is shown with an open valency on a nitrogen atom, and variables such as $R^a$, $R^b$ or $R^c$ are shown on the heteroaryl ring, such variables may be bound or joined to the open valency nitrogen. Where a chiral center exists in a structure but no specific stereochemistry is shown for the chiral center, both enantiomers associated with the chiral center are encompassed by the structure. Where a structure shown herein may exist in multiple tautomeric forms, all such tautomers are encompassed by the structure. The atoms represented in the structures herein are intended to encompass all naturally occurring isotopes of such atoms. Thus, for example, the hydrogen atoms represented herein are meant to include deuterium and tritium, and the carbon atoms are meant to include $C^{13}$ and $C^{14}$ isotopes.

Compounds of the Invention

The invention provides compounds of the formula I:

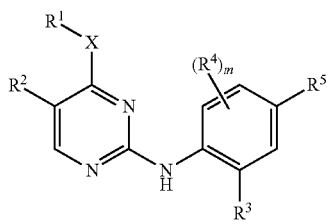

or pharmaceutically acceptable salts thereof,
wherein:
m is from 0 to 3;
X is: —$NR^a$—; —O—; or —S(O)$_r$— wherein r is from 0 to 2 and $R^a$ is hydrogen or $C_{1-6}$alkyl;
$R^1$ is: $C_{1-6}$alkyl; $C_{1-6}$alkenyl; $C_{1-6}$alkynyl; halo-$C_{1-6}$alkyl; $C_{1-6}$alkoxy-$C_{1-6}$alkyl; hydroxy-$C_{1-6}$alkyl; amino-$C_{1-6}$alkyl; $C_{1-6}$alkylsulfonyl-$C_{1-6}$alkyl; $C_{3-6}$cycloalkyl optionally substituted with $C_{1-6}$alkyl; $C_{3-6}$cycloalkyl-$C_{1-6}$alkyl wherein the $C_{3-6}$cycloalkyl portion is optionally substituted with $C_{1-6}$alkyl; tetrahydrofuranyl; tetrahydrofuranyl-$C_{1-6}$alkyl; oxetanyl; or oxetan-$C_{1-6}$alkyl;

or $R^1$ and $R^a$ together with the atoms to which they are attached may form a three to six membered ring that may optionally include an additional heteroatom selected from O, N and S, and which is substituted with oxo, halo or $C_{1-6}$alkyl;

$R^2$ is: halo; $C_{1-6}$alkoxy; cyano; $C_{1-6}$alkynyl; $C_{1-6}$alkenyl; halo-$C_{1-6}$alkyl; halo-$C_{1-6}$alkoxy; $C_{3-6}$cycloalkyl wherein the $C_{3-6}$cycloalkyl portion is optionally substituted with $C_{1-6}$alkyl; $C_{3-6}$cycloalkyl-$C_{1-6}$alkyl wherein the $C_{3-6}$cycloalkyl portion is optionally substituted with $C_{1-6}$alkyl; tetrahydrofuranyl; tetrahydrofuranyl-$C_{1-6}$alkyl; acetyl; oxetanyl; or oxetan-$C_{1-6}$alkyl;

$R^3$ and $R^4$ each independently is: halo; $C_{1-6}$alkyl; $C_{1-6}$alkoxy; $C_{3-6}$cycloalkyloxy; halo-$C_{1-6}$alkyl; or halo-$C_{1-6}$alkoxy;

or $R^3$ and $R^4$ together with the atoms to which they are attached may form a five- or six-membered ring that optionally includes one or two heteroatoms each independently selected from O, N and S, the ring being optionally substituted one or more times with $R^6$;

$R^5$ is: $C_{1-6}$alkyl-sulfonyl; $C_{3-6}$cycloalkylsulfonyl; $C_{3-6}$cycloalkyl-$C_{1-6}$alkylsulfonyl; cyano; cyano-$C_{1-6}$alkyl; heterocyclyl optionally substituted one or more times with $R^6$; heterocyclyl-$C_{1-6}$alkyl wherein the heterocyclyl moiety is optionally substituted one or more times with $R^6$; halo-$C_{1-6}$alkyl; heterocyclyl-sulfonyl wherein the heterocyclyl moiety is optionally substituted one or more times with $R^6$; or carboxy; and $R^6$ is: $C_{1-6}$alkyl; halo; halo-$C_{1-6}$alkyl; or oxo.

In certain embodiments of formula I, $R^1$ and $R^a$ together with the atoms to which they are attached may form a three to six membered ring that may optionally include an additional heteroatom selected from O, N and S, and which may be optionally substituted with oxo, halo or $C_{1-6}$alkyl.

In certain embodiments of formula I, $R^1$ and $R^a$ together with the atoms to which they are attached form a five or six membered ring.

In certain embodiments of formula I, $R^1$ and $R^a$ together with the atoms to which they are attached form a pyrolidinyl, piperidinyl or oxazoladinonyl group.

In certain embodiments of formula I, $R^2$ is acetyl.

In certain embodiments of formula I, when $R^1$ is cyclopropyl, cyclobutyl, cyclopropyl-$C_{1-6}$alkyl or cyclobutyl-$C_{1-6}$alkyl, then X is —O—.

In certain embodiments of formula I, m is from 0 to 2.
In certain embodiments of formula I, m is 0 or 1.
In certain embodiments of formula I, m is 0.
In certain embodiments of formula I, m is 1.
In certain embodiments of formula I, r is 0.
In certain embodiments of formula I, r is 2.
In certain embodiments of formula I, X is —$NR^a$—or —O—.
In certain embodiments of formula I, X is —$NR^a$.
In certain embodiments of formula I, X is —O—.
In certain embodiments of formula I, X is —S(O)$_n$—.
In certain embodiments of formula I, X is —NH—or —O—.
In certain embodiments of formula I, $R^a$ is hydrogen.
In certain embodiments of formula I, $R^a$ is $C_{1-6}$alkyl.
In certain embodiments of formula I, $R^1$ is: $C_{1-6}$alkyl; halo-$C_{1-6}$alkyl; $C_{1-6}$alkoxy-$C_{1-6}$alkyl; amino-$C_{1-6}$alkyl; $C_{1-6}$alkylsulfonyl-$C_{1-6}$alkyl; $C_{3-6}$cycloalkyl; or $C_{3-6}$cycloalkyl-$C_{1-6}$alkyl.

In certain embodiments of formula I, $R^1$ is: $C_{1-6}$alkyl; $C_{3-6}$cycloalkyl optionally substituted with $C_{1-6}$alkyl; or $C_{3-6}$cycloalkyl-$C_{1-6}$alkyl wherein the $C_{3-6}$cycloalkyl portion is optionally substituted with $C_{1-6}$alkyl.

In certain embodiments of formula I, $R^1$ is: $C_{1-6}$alkyl; halo-$C_{1-6}$alkyl; $C_{1-6}$alkoxy-$C_{1-6}$alkyl; amino-$C_{1-6}$alkyl; $C_{1-6}$alkylsulfonyl-$C_{1-6}$alkyl; tetrahydrofuranyl; tetrahydrofuranyl-$C_{1-6}$alkyl; oxetanyl; or oxetan-$C_{1-6}$alkyl.

In certain embodiments of formula I, $R^1$ is: $C_{1-6}$alkyl; halo-$C_{1-6}$alkyl; $C_{1-6}$alkoxy-$C_{1-6}$alkyl; amino-$C_{1-6}$alkyl; or $C_{1-6}$alkylsulfonyl-$C_{1-6}$alkyl.

In certain embodiments of formula I, $R^1$ is $C_{1-6}$alkyl.
In certain embodiments of formula I, $R^1$ is halo-$C_{1-6}$alkyl.
In certain embodiments of formula I, $R^1$ is $C_{1-6}$alkoxy-$C_{1-6}$alkyl.
In certain embodiments of formula I, $R^1$ is amino-$C_{1-6}$alkyl.
In certain embodiments of formula I, $R^1$ is $C_{1-6}$alkylsulfonyl-$C_{1-6}$alkyl optionally substituted with $C_{1-6}$alkyl.

In certain embodiments of formula I, $R^1$ is $C_{3-6}$cycloalkyl optionally substituted with $C_{1-6}$alkyl.

In certain embodiments of formula I, $R^1$ is $C_{3-6}$cycloalkyl-$C_{1-6}$alkyl wherein the $C_{3-6}$cycloalkyl portion is optionally substituted with $C_{1-6}$alkyl.

In certain embodiments of formula I, $R^1$ is tetrahydrofuranyl.

In certain embodiments of formula I, $R^1$ is tetrahydrofuranyl-$C_{1-6}$alkyl; oxetanyl.

In certain embodiments of formula I, $R^1$ is or oxetan-$C_{1-6}$alkyl.

In certain embodiments of formula I, $R^1$ is: methyl; ethyl; n-propyl; isopropyl; isobutyl; 3,3-dimethylpropyl; cyclopropyl; cyclobutyl; cyclopentyl; cyclohexyl; cyclopropylmethyl; cyclobutylmethyl; cyclopentylmethyl; cyclopropylethyl; methoxyethyl; oxetanyl; or tetrahydrofuranylmethyl.

In certain embodiments of formula I, $R^1$ is: methyl; ethyl; n-propyl; isopropyl; isobutyl; 3,3-dimethylpropyl; cyclopentyl; cyclohexyl; cyclopropylmethyl; cyclobutylmethyl; cyclopentylmethyl; cyclopropylethyl; methoxyethyl; oxetanyl; or tetrahydrofuranylmethyl.

In certain embodiments of formula I, $R^1$ is: methyl; ethyl; n-propyl; isopropyl; isobutyl; 3,3-dimethylpropyl; cyclopentyl; cyclohexyl; cyclopentylmethyl; methoxyethyl; oxetanyl; or tetrahydrofuranylmethyl.

In certain embodiments of formula I, $R^1$ is: methyl; ethyl; n-propyl; isopropyl; or isobutyl.

In certain embodiments of formula I, $R^1$ is methyl or ethyl.

In certain embodiments of formula I, $R^1$ is methyl.

In certain embodiments of formula I, $R^1$ is ethyl.

In certain embodiments of formula I, $R^1$ is: cyclopropyl; cyclobutyl; cyclopentyl; cyclohexyl; cyclopropylmethyl; cyclobutylmethyl; cyclopentylmethyl; or cyclopropylethyl.

In certain embodiments of formula I, $R^1$ is: cyclopentyl; cyclohexyl; or cyclopentylmethyl.

In certain embodiments of formula I, $R^2$ is: halo; $C_{1-6}$alkoxy; halo-$C_{1-6}$alkyl; halo-$C_{1-6}$alkoxy; $C_{3-6}$cycloalkyl wherein the $C_{3-6}$cycloalkyl portion is optionally substituted with $C_{1-6}$alkyl; $C_{3-6}$cycloalkyl-$C_{1-6}$alkyl wherein the $C_{3-6}$cycloalkyl portion is optionally substituted with $C_{1-6}$alkyl; tetrahydrofuranyl; tetrahydrofuranyl-$C_{1-6}$alkyl; oxetanyl; or oxetan-$C_{1-6}$alkyl.

In certain embodiments of formula I, $R^2$ is: halo; $C_{1-6}$alkoxy; halo-$C_{1-6}$alkyl; cyano; $C_{1-6}$alkynyl; $C_{1-6}$alkenyl; $C_{3-6}$cycloalkyl; or $C_{3-6}$cycloalkyl-$C_{1-6}$alkyl.

In certain embodiments of formula I, $R^2$ is: halo; $C_{1-6}$alkoxy; halo-$C_{1-6}$alkyl; cyano; $C_{3-6}$cycloalkyl; or $C_{3-6}$cycloalkyl-$C_{1-6}$alkyl.

In certain embodiments of formula I, $R^2$ is: halo; $C_{1-6}$alkoxy; halo-$C_{1-6}$alkyl; $C_{3-6}$cycloalkyl; or $C_{3-6}$cycloalkyl-$C_{1-6}$alkyl.

In certain embodiments of formula I, $R^2$ is: halo; halo-$C_{1-6}$alkyl; or cyano.

In certain embodiments of formula I, $R^2$ is: halo; or halo-$C_{1-6}$alkyl.

In certain embodiments of formula I, $R^2$ is halo.

In certain embodiments of formula I, $R^2$ is $C_{1-6}$alkoxy.

In certain embodiments of formula I, $R^2$ is halo-$C_{1-6}$alkoxy.

In certain embodiments of formula I, $R^2$ is halo-$C_{1-6}$alkyl.

In certain embodiments of formula I, $R^2$ is $C_{3-6}$cycloalkyl.

In certain embodiments of formula I, $R^2$ is $C_{3-6}$cycloalkyl-$C_{1-6}$alkyl.

In certain embodiments of formula I, $R^2$ is tetrahydrofuranyl.

In certain embodiments of formula I, $R^2$ is tetrahydrofuranyl-$C_{1-6}$alkyl.

In certain embodiments of formula I, $R^2$ is oxetanyl.

In certain embodiments of formula I, $R^2$ is oxetan-$C_{1-6}$alkyl.

In certain embodiments of formula I, $R^2$ is halo, trifluoromethyl or cyano.

In certain embodiments of formula I, $R^2$ is chloro, trifluoromethyl or cyano.

In certain embodiments of formula I, $R^2$ is chloro or trifluoromethyl.

In certain embodiments of formula I, $R^2$ is fluoro, chloro or bromo.

In certain embodiments of formula I, $R^2$ is chloro.

In certain embodiments of formula I, $R^2$ is fluoro.

In certain embodiments of formula I, $R^2$ is bromo.

In certain embodiments of formula I, $R^2$ is trifluoromethyl.

In certain embodiments of formula I, $R^2$ is methoxy.

In certain embodiments of formula I, $R^2$ is cyano.

In certain embodiments of formula I, $R^2$ is $C_{1-6}$alkynyl.

In certain embodiments of formula I, $R^2$ is $C_{1-6}$alkenyl.

In certain embodiments of formula I, $R^3$ is: $C_{1-6}$alkyl;

In certain embodiments of formula I, $R^3$ is halo.

In certain embodiments of formula I, $R^3$ is $C_{1-6}$alkyl.

In certain embodiments of formula I, $R^3$ is $C_{1-6}$alkoxy.

In certain embodiments of formula I, $R^3$ is halo or $C_{1-6}$alkoxy.

In certain embodiments of formula I, $R^3$ is $C_{3-6}$cycloalkyloxy.

In certain embodiments of formula I, $R^3$ is halo-$C_{1-6}$alkyl.

In certain embodiments of formula I, $R^3$ is halo-$C_{1-6}$alkoxy.

In certain embodiments of formula I, $R^3$ is halo or methoxy.

In certain embodiments of formula I, $R^3$ is fluoro, chloro or methoxy.

In certain embodiments of formula I, $R^3$ is fluoro or chloro.

In certain embodiments of formula I, $R^3$ is methoxy.

In certain embodiments of formula I, $R^3$ is methyl

In certain embodiments of formula I, $R^3$ is chloro.

In certain embodiments of formula I, $R^3$ is fluoro.

In certain embodiments of formula I, $R^4$ is: $C_{1-6}$alkyl;

In certain embodiments of formula I, $R^4$ is halo.

In certain embodiments of formula I, $R^4$ is $C_{1-6}$alkyl.

In certain embodiments of formula I, $R^4$ is $C_{1-6}$alkoxy.

In certain embodiments of formula I, $R^4$ is halo-$C_{1-6}$alkyl.

In certain embodiments of formula I, $R^4$ is halo-$C_{1-6}$alkoxy.

In certain embodiments of formula I, $R^4$ is halo or methoxy.

In certain embodiments of formula I, $R^4$ is $R^4$ is fluoro, chloro, methyl or methoxy.

In certain embodiments of formula I, $R^4$ is fluoro, chloro or methoxy.

In certain embodiments of formula I, $R^4$ is fluoro or chloro.

In certain embodiments of formula I, $R^4$ is methoxy.

In certain embodiments of formula I, $R^4$ is methyl

In certain embodiments of formula I, $R^4$ is chloro.

In certain embodiments of formula I, $R^4$ is fluoro.

In certain embodiments of formula I, $R^4$ is $C_{3-6}$cycloalkyloxy.

In certain embodiments of formula I, $R^3$ and $R^4$ together with the atoms to which they are attached form a five- or six-membered ring that optionally includes one or two heteroatoms each independently selected from O, N and S, the ring being optionally substituted one or more times with $R^6$.

In certain embodiments of formula I, $R^3$ and $R^4$ together with the atoms to which they are attached form a six-membered ring that includes two oxygen atoms separated by an ethylene group (i.e., $R^3$ and $R^4$ together form an ethylenedioxy group).

In certain embodiments of formula I, $R^3$ and $R^4$ together with the atoms to which they are attached form a five-membered ring that includes two oxygen atoms separated by a methylene group (i.e., $R^3$ and $R^4$ together form a methylenedioxy group).

In certain embodiments of formula I, $R^5$ is $C_{1-6}$alkyl-sulfonyl.

In certain embodiments of formula I, $R^5$ is $C_{1-6}$alkyl-sulfonyl or cyano.

In certain embodiments of formula I, $R^5$ is $C_{3-6}$cycloalkyl-sulfonyl.

In certain embodiments of formula I, $R^5$ is cyano.

In certain embodiments of formula I, $R^5$ is cyano-$C_{1-6}$alkyl.

In certain embodiments of formula I, $R^5$ is heterocyclyl optionally substituted with $R^6$.

In certain embodiments of formula I, $R^5$ is heterocyclyl-$C_{1-6}$alkyl wherein the heterocyclyl moiety is optionally substituted with $R^6$.

In certain embodiments of formula I, $R^5$ is halo-$C_{1-6}$alkyl.

In certain embodiments of formula I, $R^5$ is carboxy.

In certain embodiments of formula I, $R^5$ is methanesulfonyl.

In certain embodiments of formula I, $R^5$ is morpholin-4-yl-methyl.

In certain embodiments of formula I, $R^5$ is morpholinyl.

In certain embodiments of formula I, $R^5$ is morpholin-4-yl.

In certain embodiments of formula I, $R^5$ is oxetanyl.

In certain embodiments of formula I, $R^5$ is oxetan-3-yl.

In certain embodiments of formula I, $R^5$ is pyrrolidinonyl.

In certain embodiments of formula I, $R^5$ is pyrrolidin-2-one-1-yl.

In certain embodiments of formula I, $R^5$ is motpholinonyl.

In certain embodiments of formula I, $R^5$ is morpholin-3-one-4-yl.

In certain embodiments of formula I, $R^5$ is piperidinonyl.

In certain embodiments of formula I, $R^5$ is piperidin-2-one-1-yl.

In certain embodiments of formula I, $R^5$ is trifluoromethyl

In certain embodiments of formula I, $R^5$ is heterocyclysulfonyl wherein the heterocyclyl moiety is optionally substituted one or more times with $R^6$.

In certain embodiments of formula I, $R^5$ is morpholin-4-sulfonyl.

In certain embodiments of formula I, $R^5$ is morpholin-sulfonyl.

In embodiments of the invention whererin $R^5$ is heterocyclyl or contains a heterocyclyl moiety, such heterocyclyl may be azepinyl, piperidinyl, piperazinyl, morpholinyl, thiomorpholinyl, tetrahydropyranyl, pyrrolidinyl, tetrahydrofuranyl, azetidinyl or oxetanyl, each optionally substituted one or more times with $R^6$.

In embodiments of the invention whererin $R^5$ is heterocyclyl or contains a heterocyclyl moiety, such heterocyclyl may be piperidinyl, piperazinyl, morpholinyl, thiomorpholinyl, tetrahydropyranyl, tetrahydrofuranyl, oxetanyl, azetidinyl, azepinyl, oxazepinyl, or pyrrolidinyl, each optionally substituted one or more times with $R^6$.

In embodiments of the invention whererin $R^5$ is heterocyclyl or contains a heterocyclyl moiety, such heterocyclyl may be piperidinyl, piperazinyl, morpholinyl, thiomorpholinyl, or pyrrolidinyl, each optionally substituted one or more times with $R^6$.

In certain embodiments of formula I, $R^5$ is: methanesulfonyl; cyano; morpholin-4-yl-methyl; morpholin-4-yl; morpholin-4-yl-sulfonyl; or trifluoromethyl.

In certain embodiments of formula I, $R^5$ is: methanesulfonyl; cyano; or morpholin-4-yl-methyl.

In certain embodiments of formula I, $R^5$ is: methanesulfonyl; or cyano.

Where any of $R^1$, $R^2$, $R^3$, $R^4$ and $R^5$, is alkyl or contains an alkyl moiety, such alkyl may be lower alkyl, i.e. $C_1$-$C_6$alkyl, and in many embodiments may be $C_1$-$C_4$alkyl.

The invention also provides a method for treating a disease or condition mediated by or otherwise associated with the LRRK2 receptor, the method comprising administering to a subject in need thereof an effective amount of a compound of the invention.

The disease may be a neurodegenerative disease such as Parkinson's disease, Huntington's disease or Lewie body dementia.

The disease may be a CNS disorder such as Alzheimer's disease and L-Dopa induced dyskinesia.

The disease may be a cancer or proliferative disorder such as kidney, breast, prostate, blood, papillary or lung cancer, acute myelogenous leukemia, or multiple myeloma.

The disease may be an inflammatory disease such as leprosy, Crohn's disease, amyotrophic lateral sclerosis, rheumatoid arthritis, and ankylosing spondylytis.

The invention also provides a method for enhancing cognitive memory, the method comprising administering to a subject in need thereof an effective amount of a compound of the invention.

Representative compounds in accordance with the methods of the invention are shown in the experimental examples below.

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis;* Wiley & Sons: New York, 1991, Volumes 1-15; *Rodd's Chemistry of Carbon Compounds,* Elsevier Science Publishers, 1989, Volumes 1-5 and Supplementals; and *Organic Reactions,* Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein may be conducted under an inert atmosphere at atmospheric pressure at a reaction temperature range of from about −78° C. to about 150° C., for example, from about 0° C. to about 125° C., or conveniently at about room (or ambient) temperature, e.g., about 20° C.

Scheme A below illustrates one synthetic procedure usable to prepare specific compounds of formula I or formula II, wherein X, m, $R^1$, $R^2$, $R^3$, $R^4$ and $R^5$ are as defined herein.

SCHEME A

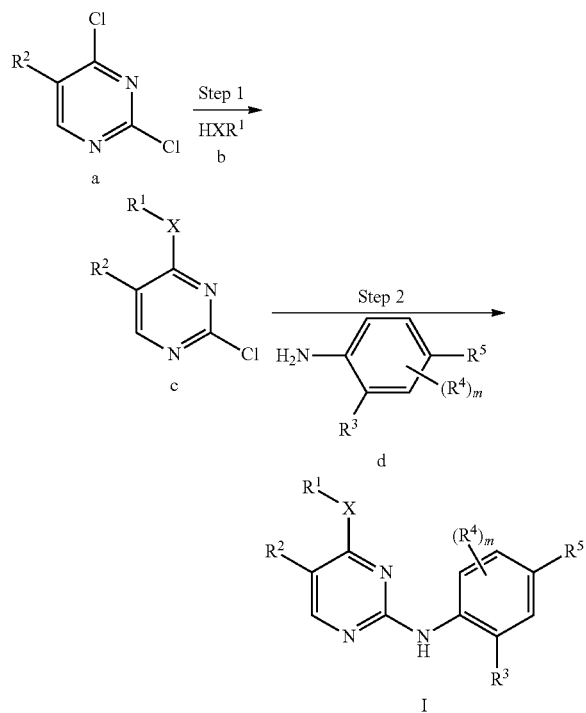

In step 1 of Scheme A, dichloropyrimidine compound a is reacted with reagent b to afford pyrimidine compound c. The reaction of step 1 may take place under polar solvent conditions. In embodiments of the invention where X is —O— (i.e., reagent b is an alcohol), the reaction of step 1 may be carried out in the presence of base.

In step 2, pyrimidine compound c undergoes reaction with aniline compound d to provide a phenylaminopyridine compound of formula I in accordance with the invention. The reaction of step 2 may take place in polar protic solvent and in the presence of acid such as HCl. Many aniline compound d are commercially available or can be easily prepared from nitrobenzenes as shown in the Examples below.

Many variations on the procedure of Scheme A are possible and will suggest themselves to those skilled in the art. Specific details for producing compounds of the invention are described in the Examples below.

Administration and Pharmaceutical Composition

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, for example 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. A particular manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets may contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations may be in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described below.

Utility

The compounds of the invention are useful for treatment of LRRK2-mediated diseases or conditions, including neurodegenerative diseases such as Parkinson's disease, Lewy body dementia and Huntington's disease, and for enhancemenent of cognitive memory generally in subjects in need thereof.

EXAMPLES

The following preparations and examples are given to enable those skilled in the art to more clearly understand and to practice the present invention. They should not be considered as limiting the scope of the invention, but merely as being illustrative and representative thereof.

Unless otherwise stated, all temperatures including melting points (i.e., MP) are in degrees celsius (° C.). It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product. The following abbreviations may be used in the Preparations and Examples.

List of Abbreviations
AcOH Acetic acid
AIBN 2,2'-Azobis(2-methylpropionitrile)
Atm. Atmosphere
(BOC)$_2$O di-tert-Butyl dicarbonate
DavePhos 2-Dicyclohexylphosphino-2'-(N,N-dimethylamino)biphenyl
DCM Dichloromethane/Methylene chloride
DIAD Diisopropyl azodicarboxylate
DIPEA Diisopropylethylamine
DMAP 4-Dimethylaminopyridine
DME 1,2-Dimethoxyethane
DMF N,N-Dimethylformamide
DMSO Dimethyl sulfoxide
DPPF 1,1'-Bis(diphenylphosphino)ferrocene
Et$_2$O Diethyl ether
EtOH Ethanol/Ethyl alcohol
EtOAc Ethyl acetate
HATU 2-(1H-7-Azabenzotriazol-1-yl)-1,1,3,3-tetramethyl uronium hexafluorophosphate Methanaminium
HBTU O-Benzotriazol-1-yl-N,N,N',N'-tetramethyluronium hexafluorophosphate
HOBT 1-Hydroxybenzotriazole
HPLC High pressure liquid chromatography
RP HPLC Reverse phase high pressure liquid chromatography
i-PrOH Isopropanol/isopropyl alcohol
LCMS Liquid Chromatograph/Mass Spectroscopy
MeOH Methanol/Methyl alcohol
MW Microwaves
NBS N-Bromosuccinimide
NMP 1-Methyl-2-pyrrolidinone
PSI Pound per square inch
RT Room temperature
TBDMS tert-Butyldimethylsilyl
TFA Trifluoroacetic acid
THF Tetrahydrofuran
TLC Thin layer chromatography Preparation 1:
2-chloro-5-fluoro-N-methylpyrimidin-4-amine

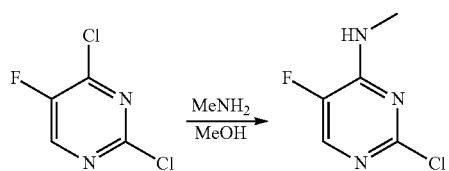

To a 250 mL round bottom flask equipped with a stir bar was added 9.0 g 5-fluoro-2,4-dichloro-pyrimidine, 40 mL methanol and 15 mL of 8M methylamine in ethanol. The reaction heated up (mild exo-therm) and was allowed to stir at room temperature for ~30 minutes. A check by TLC (1:1 EtOAc: heptane) and LCMS showed complete reaction. The reaction was concentrated down to give 9.77 g crude material which was purified on a silica column running a gradient of 1% to 10% MeOH in DCM over 35 minutes to give 6.77 g pure 2-chloro-5-fluoro-N-methylpyrimidin-4-amine.

The same method was used to make the compounds shown in Table 1 below, using the appropriate commercially available substituted 2,4-dichloro-pyrimidines and amines.

TABLE 1

| | | |
|---|---|---|
| 1 | 2-chloro-5-chloro-N-methylpyrimidin-4-amine | |
| 2 | 2-chloro-5-bromo-N-methylpyrimidin-4-amine | |
| 3 | 2-chloro-5-trifluoromethyl-N-methylpyrimidin-4-amine | |
| 6 | 2-chloro-5-methoxy-N-methylpyrimidin-4-amine | |
| 8 | 2-chloro-5-fluoro-N,N-dimethylpyrimidin-4-amine | |
| 9 | 2-chloro-5-chloro-N-ethylpyrimidin-4-amine | |
| 10 | 2-chloro-5-chloro-N-propylpyrimidin-4-amine | |

TABLE 1-continued

| | | |
|---|---|---|
| 11 | 2-chloro-5-chloro-N-isopropylpyrimidin-4-amine | |
| 12 | 2-chloro-5-chloro-N-isobutylpyrimidin-4-amine | |
| 13 | 4-(2,5-dichloropyrimidin-4-yl)morpholine | |
| 14 | 2,5-dichloropyrimidin-4-amine | |
| 15 | 2,5-dichloro-N,N-dimethylpyrimidin-4-amine | |
| 16 | 4-(azetidin-1-yl)-2,5-dichloropyrimidine | |
| 17 | 2,5-dichloro-4-(pyrrolidin-1-yl)pyrimidine | |
| 18 | 2,5-dichloro-4-(piperidin-1-yl)pyrimidine | |
| 19 | 2,5-dichloro-4-(2-(methoxymethyl)piperidin-1-yl)pyrimidine | |
| 20 | 2,5-dichloro-4-(4-(methoxymethyl)piperidin-1-yl)pyrimidine | |
| 21 | 2,5-dichloro-N-(cyclopropylmethyl)pyrimidin-4-amine | |
| 22 | 2,5-dichloro-N-(cyclobutylmethyl)pyrimidin-4-amine | |
| 23 | 2,5-dichloro-N-(cyclopentylmethyl)pyrimidin-4-amine | |
| 24 | 2-chloro-N-methylpyrimidin-4-amine | |

TABLE 1-continued

| 25 | 2,5-dichloro-N-(2-methoxyethyl)pyrimidin-4-amine | |
|----|---|---|

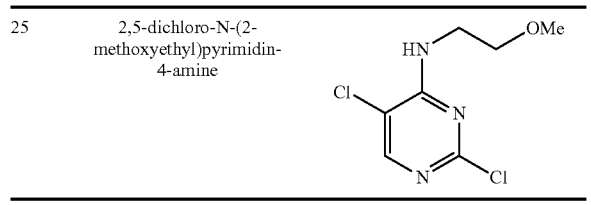

Preparation 2: 2,5-dichloro-4-methoxypyrimidine

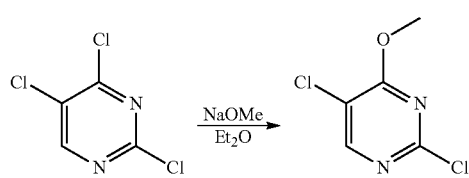

To a 250 mL round bottom flask equipped with a stir bar was added 1 g 5-chloro-2,4-dichloro-pyrimidine, and 15 mL of diethyl ether. The mixture was cooled to 0° C. in an ice bath and then 1 equivalent of sodium methoxide in methanol (prepared from reacting 120 mg of sodium with 4 mL of methanol at room temperature) was slowly added. The reaction was stirred overnight at room temperature and checked by LCMS. The white precipitate was filtered and the solid washed with cold methanol. After drying, 0.98 g of pure 2,5-dichloro-4-methoxypyrimidine was obtained and this material was used without further purification.

The same method was used to make the compounds shown in Table 2 below, using the appropriate commercially available alcohols and the appropriately substituted 2,4-dichloro-pyrimidines.

TABLE 2

| 1 | 2,5-dichloro-4-ethoxypyrimidine | |
|---|---|---|
| | | 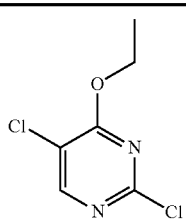 |
| 2 | 2,5-dichloro-4-propoxypyrimidine | |
| | | 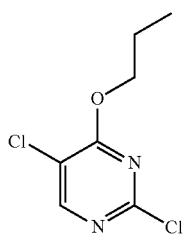 |
| 3 | 2,5-dichloro-4-isoprpoxypyrimidine | |
| | | 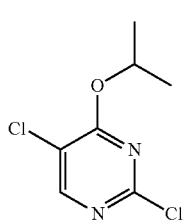 |

TABLE 2-continued

| 6 | 5-bromo-2-chloro-4-methoxypyrimidine | |
|---|---|---|
| | | |
| 7 | 2-chloro-iodo-4-methoxypyrimidine | |

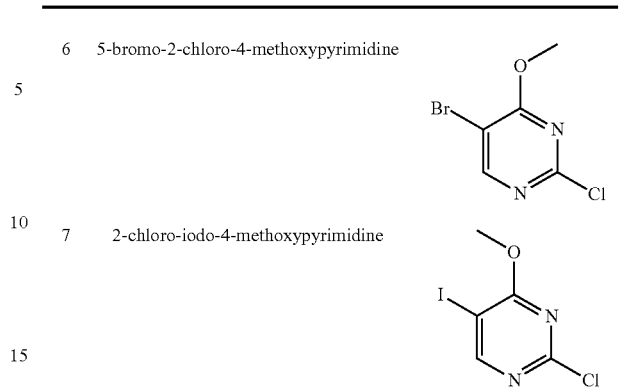

Preparation 3: 2-Methoxy-4-(methylsulfonyl)aniline

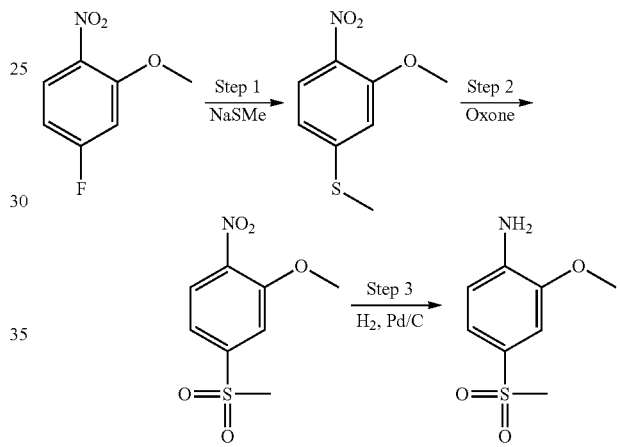

Step 1: 2-Methoxy-4-(methylsulfonyl)aniline

A mixture of 4-fluoro-2-methoxy-1-nitrobenzene (1.38 g, 8.06 mmol) and sodium methyl mercaptide (0.622 g, 8.87 mmol) in DMF (25 mL) was stirred at room temperature for 18 hours. The reaction was the diluted with water and extracted with EtOAc. The combined extracts were washed with brine, dried over sodium sulfate, filtered and concentrated to give (3-methoxy-4-nitrophenyl)(methyl)sulfane (0.95 g, 59%).

Step 2: 2-Methoxy-4-(methylsulfonyl)-1-nitrobenzene

To a suspension of (3-methoxy-4-nitrophenyl)(methyl)sulfane (0.58 g, 2.9 mmol) in acetone (10 mL) was added water (10 mL), methanol (1.0 mL). The mixture was cooled in an ice-bath for 10 minutes before adding Oxone (2.90 g, 4.72 mmol) in four portions over 4 minutes. The reaction was stirred at 0° C. for 15 minutes and then allowed to warm up to room temperature. The reaction was stirred at room temperature for 2 hours before being diluted with EtOAc (50 mL). The suspension was filtered, concentrated to ⅓ of its volume and diluted with water (40 mL). The mixture was then extracted with EtOAc. The combined extracts were washed with brine, dried over sodium sulfate, filtered and concentrated to give 2-methoxy-4-(methylsulfonyl)-1-nitrobenzene (0.67 g, 83%).

Step 3: 2-Methoxy-4-(methylsulfonyl)aniline

A suspension of 2-methoxy-4-(methylsulfonyl)-1-nitrobenzene (0.175 g, 0.76 mmol) and palladium on carbon (10 wt %, 0.10 g) in ethanol (10 mL) was stirred under hydrogen at one atmosphere pressure for 18 hours. The reaction was filtered through celite and concentrated to give 2-methoxy-4-(methylsulfonyl)aniline (0.15 g, 92%).

Similarly prepared were: 2-chloro-4-(methylsulfonyl) aniline; 5-fluoro-2-methoxy-4-(methylsulfonyl)aniline; 2-isopropoxy-4-(methylsulfonyl)aniline; 2-(2-fluoroethoxy)-4-(methylsulfonyl)aniline; 5-chloro-2-methoxy-4-(methylsulfonyl)aniline; and 2-methoxy-5-methyl-4-(methylsulfonyl)aniline.

Preparation 4:
4-Amino-2-fluoro-5-methoxybenzonitrile

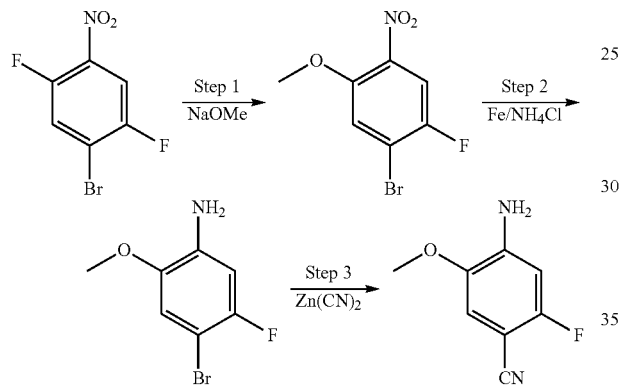

Step 1: 1-Bromo-2-fluoro-5-methoxy-4-nitrobenzene

To a solution of 1-bromo-2,5-difluoro-4-nitrobenzene (2.56 g, 0.011 mmol) in methanol (20 mL) was added a 25% sodium methoxide in methanol solution (2.5 mL). The mixture was stirred at room temperature for 1.5 hours. The reaction was then concentrated, re-dissolved in EtOAc and washed with water. The aqueous wash was back-extracted with EtOAc. The combined organic extracts were washed with brine, dried over sodium sulfate, filtered and concentrated to give 1-bromo-2-fluoro-5-methoxy-4-nitrobenzene (2.65 g, 99%).

Step 2: 4-Bromo-5-fluoro-2-methoxyaniline

To a solution of 1-bromo-2-fluoro-5-methoxy-4-nitrobenzene (0.998 g, 3.99 mmol) in isopropanol (20 mL) was added iron (0.7 g, 12 mmol), ammonium chloride (0.64 g, 12 mmol) and water (2 mL). The reaction was stirred at 75° C. for 2 hours, then filtered and concentrated. The residue was diluted with water and extracted with EtOAc. The combined organic extracts were washed with brine, dried over sodium sulfate, filtered and concentrated to give 4-bromo-5-fluoro-2-methoxyaniline (0.82 g, 93%).

Step 3: 4-Amino-2-fluoro-5-methoxybenzonitrile

To a pressure tube was added 4-bromo-5-fluoro-2-methoxyaniline (0.24 g, 1.1 mmol), zinc cyanide (0.10 g, 0.87 mmol), $Pd_2(dba)_3$ (100 mg, 0.11 mmol), DavePhos (86 mg, 0.22 mmol) and DMF (3 mL). The reaction was sealed and stirred at 100° C. for 6 hours. The reaction was diluted with water and extracted with EtOAc. The combined organic extracts were washed with brine, dried over sodium sulfate, filtered and concentrated. The crude product was purified by flash chromatography to give 4-amino-2-fluoro-5-methoxybenzonitrile (0.18 g, 77%).

Similarly prepared were: 4-amino-5-chloro-2-methylbenzonitrile; 4-amino-5-methoxy-2-methylbenzonitrile; and 4-amino-3-methoxybenzonitrile.

EXAMPLE 1

N2-(2-Methoxy-4-(methylsulfonyl)phenyl)-N4-methyl-5-(trifluoromethyl)pyrimidine-2,4-diamine

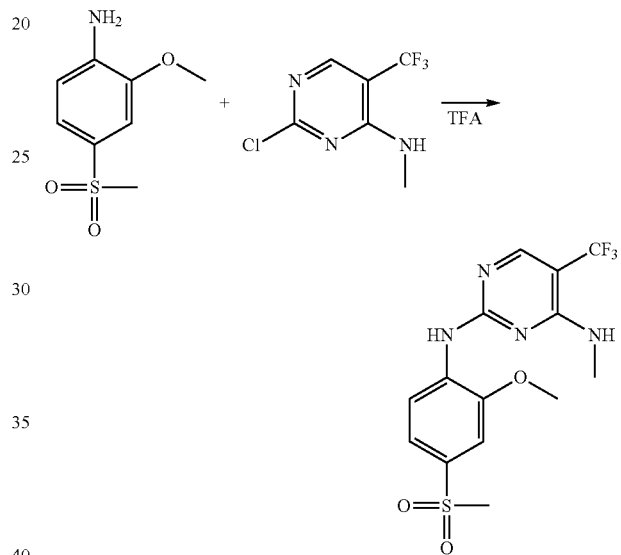

To a mixture of 2-methoxy-4-(methylsulfonyl)aniline (0.095 g, 0.47 mmol) and 2-chloro-N-methyl-5-(trifluoromethyl)pyrimidin-4-amine (0.10 g, 0.47 mmol) in 1-butanol (1.5 mL) was added TFA (0.036 mL, 0.047 mmol). The reaction was stirred in a sealed tube at 100° C. for 1.5 h. The reaction was concentrated and the product was isolated by reverse-phase HPLC to give N2-(2-methoxy-4-(methylsulfonyl)phenyl)-N4-methyl-5-(trifluoromethyl)pyrimidine-2,4-diamine (0.18 g, 20%). 1H NMR (400 MHz, DMSO) δ 8.58 (d, J=12.9, 1H), 8.24 (d, J=5.0, 2H), 7.53 (d, J=10.1, 1H), 7.48 (s, 1H), 7.38-7.29 (m, 1H), 3.99 (s, 3H), 3.20 (s, 3H), 2.94 (d, J=4.3, 3H); LRRK2 Ki=0.002.

EXAMPLE 2

5-Chloro-N2-(2-methoxy-4-(methylsulfonyl)phenyl)-N4-methylpyrimidine-2,4-diamine Similarly prepared, using 2-chloro-5-chloro-N-methylpyrimidin-4-amine in place of 2-chloro-N-methyl-5-(trifluoromethyl)pyrimidin-4-amine, was 5-chloro-N2-(2-methoxy-4-(methylsulfonyl)phenyl)-N4-methylpyrimidine-2,4-diamine; 1H NMR (400 MHz, DMSO) δ 8.64 (d, J=8.6, 1H), 8.01 (s, 1H), 7.86 (s, 1H), 7.51 (d, J=8.6, 1H), 7.45 (s, 1H), 7.42 (d, J=4.3, 1H), 3.99 (s, 3H), 3.18 (s, 3H), 2.93 (d, J=4.5, 3H); LRRK2 Ki=0.002.

Additional compounds prepared using the above procedures are shown in Table 3 below, together with LRRK2 K$_i$ (micromolar) affinity values for selected compounds.

EXAMPLE 3

2-Fluoro-5-methoxy-4-(4-(methylamino)-5-(trifluoromethyl)pyrimidin-2-ylamino)benzonitrile

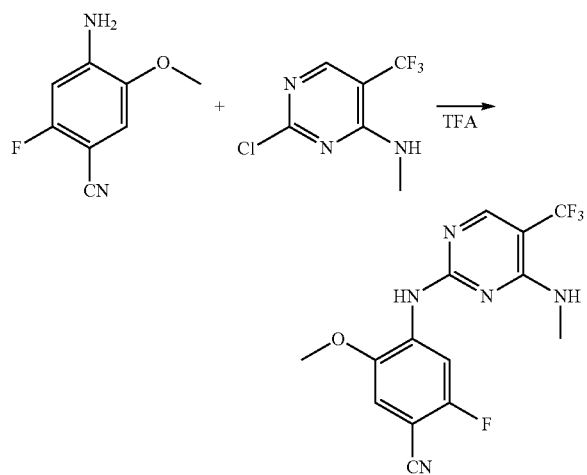

To a mixture of 4-amino-2-fluoro-5-methoxybenzonitrile (66 mg, 0.40 mmol) and 2-chloro-N-methyl-5-(trifluoromethyl)pyrimidin-4-amine (0.10 g, 0.47 mmol) in 1-butanol (2 mL) was added TFA (0.05 mL, 0.07 mmol). The reaction was stirred in a sealed tube at 75° C. for 2 h. The reaction was concentrated and the product was isolated by reverse-phase HPLC to give 2-fluoro-5-methoxy-4-(4-(methylamino)-5-(trifluoromethyl)pyrimidin-2-ylamino)benzonitrile. 1H NMR (400 MHz, DMSO) δ 8.57 (d, J=13.4, 2H), 8.34 (s, 1H), 8.29 (d, J=6.1, 1H), 7.56-7.42 (m, 3H), 3.93 (s, 3H), 2.95 (s, 3H); LRRK2 Ki=0.022.

EXAMPLE 4

3-Methoxy-4-(4-(methylamino)-5-(trifluoromethyl)pyrimidin-2-ylamino)benzonitrile Similarly prepared, using 4-amino-3-methoxybenzonitrile in place of 4-amino-2-fluoro-5-methoxybenzonitrile, was :3-methoxy-4-(4-(methylamino)-5-(trifluoromethyl)pyrimidin-2-ylamino)benzonitrile: 1H NMR (400 MHz, DMSO) δ 8.53 (d, J=8.7, 1H), 8.23 (d, J=8.4, 1H), 7.49 (s, 1H), 7.45 (d, J=8.0, 1H), 7.35 (dd, J=12.3, 7.3, 1H), 3.94 (s, 3H), 2.93 (d, J=4.4, 3H); LRRK2 Ki=0.008.

EXAMPLE 5

4-(5-Chloro-4-(methylamino)pyrimidin-2-ylamino)-3-methoxybenzonitrile

Similarly prepared, using 4-amino-3-methoxybenzonitrile in place of 4-amino-2-fluoro-5-methoxybenzonitrile, and 5-chloro-N4-methylpyrimidine-2,4-diamine in place of 2-chloro-N-methyl-5-(trifluoromethyl)pyrimidin-4-amine, was 4-(5-chloro-4-(methylamino)pyrimidin-2-ylamino)-3-methoxybenzonitrile: 1H NMR (400 MHz, DMSO) δ 8.59 (d, 1H), 8.01 (s, 1H), 7.86 (s, 1H), 7.42 (m, 3H), 3.94 (s, 3H), 2.92 (d, 3H); LRRK2 Ki=0.008.

Additional compounds prepared using the above procedures are shown in Table 3 below, together with LRRK2 K$_i$ (micromolar) affinity values for selected compounds.

TABLE 3

| | Structure | Name | K$_i$ |
|---|---|---|---|
| 6 | 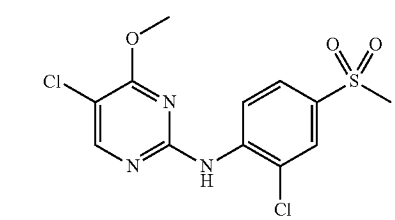 [SMILES: COc1nc(Nc2ccc(S(C)(=O)=O)cc2Cl)ncc1Cl] | (2-Chloro-4-methanesulfonyl-phenyl)-(5-chloro-4-methoxy-pyrimidin-2-yl)-amine | 0.061 |
| 7 | 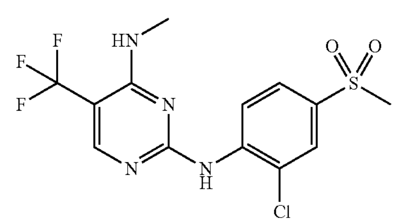 [SMILES: CNc1nc(Nc2ccc(S(C)(=O)=O)cc2Cl)ncc1C(F)(F)F] | N2-(2-Chloro-4-methanesulfonyl-phenyl)-N4-methyl-5-trifluoromethyl-pyrimidine-2,4-diamine | 0.008 |
| 8 | 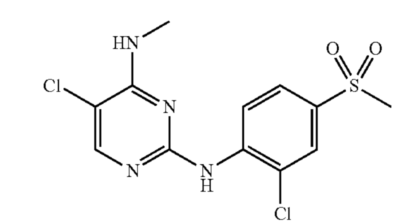 | 5-Chloro-N2-(2-chloro-4-methanesulfonyl-phenyl)-N4-methyl-pyrimidine-2,4-diamine | 0.008 |

TABLE 3-continued

| | Structure | Name | $K_i$ |
|---|---|---|---|
| 9 | 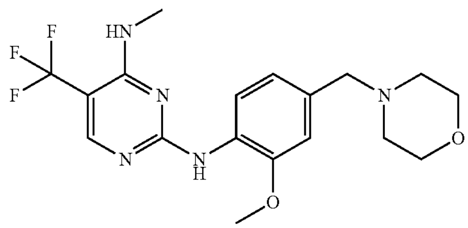 [SMILES: CNc1nc(Nc2ccc(CN3CCOCC3)cc2OC)ncc1C(F)(F)F] | N2-(2-Methoxy-4-morpholin-4-ylmethyl-phenyl)-N4-methyl-5-trifluoromethyl-pyrimidine-2,4-diamine | 0.003 |
| 10 | 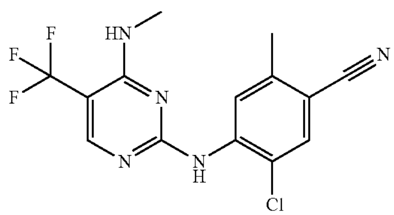 [SMILES: CNc1nc(Nc2cc(C)c(C#N)cc2Cl)ncc1C(F)(F)F] | 5-Chloro-2-methyl-4-(4-methylamino-5-trifluoromethyl-pyrimidin-2-ylamino)-benzonitrile | 0.046 |
| 11 | 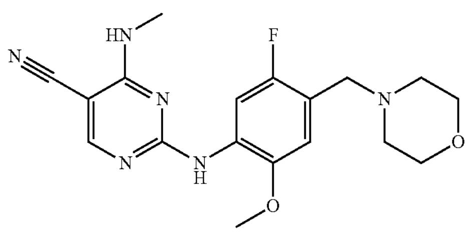 [SMILES: CNc1nc(Nc2cc(F)c(CN3CCOCC3)cc2OC)ncc1C#N] | 2-(5-Fluoro-2-methoxy-4-morpholin-4-ylmethyl-phenylamino)-4-methylamino-pyrimidine-5-carbonitrile | 0.027 |
| 12 | 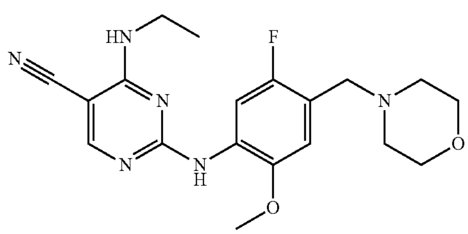 [SMILES: CCNc1nc(Nc2cc(F)c(CN3CCOCC3)cc2OC)ncc1C#N] | 4-Ethylamino-2-(5-fluoro-2-methoxy-4-morpholin-4-ylmethyl-phenylamino)-pyrimidine-5-carbonitrile | 0.014 |
| 13 | 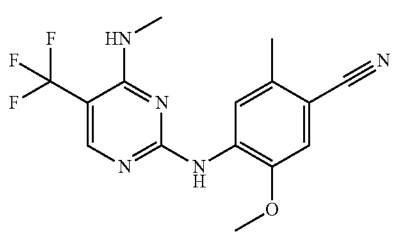 [SMILES: CNc1nc(Nc2cc(C)c(C#N)cc2OC)ncc1C(F)(F)F] | 5-Methoxy-2-methyl-4-(4-methylamino-5-trifluoromethyl-pyrimidin-2-ylamino)-benzonitrile | 0.012 |
| 14 | 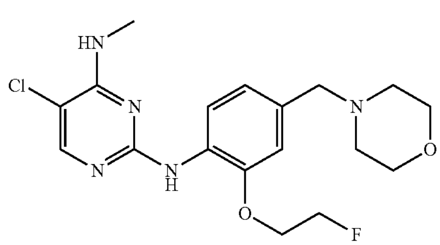 [SMILES: CNc1nc(Nc2ccc(CN3CCOCC3)cc2OCCF)ncc1Cl] | 5-Chloro-N2-[2-(2-fluoro-ethoxy)-4-morpholin-4-ylmethyl-phenyl]-N4-methyl-pyrimidine-2,4-diamine | 0.009 |

TABLE 3-continued

| | Structure | Name | $K_i$ |
|---|---|---|---|
| 15 | 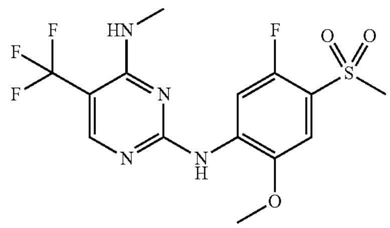 [SMILES: CNc1nc(Nc2cc(F)c(S(C)(=O)=O)cc2OC)ncc1C(F)(F)F] | N2-(5-Fluoro-4-methanesulfonyl-2-methoxy-phenyl)-N4-methyl-5-trifluoromethyl-pyrimidine-2,4-diamine | 0.003 |
| 16 | 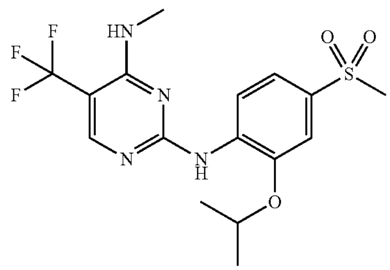 [SMILES: CNc1nc(Nc2ccc(S(C)(=O)=O)cc2OC(C)C)ncc1C(F)(F)F] | N2-(2-Isopropoxy-4-methanesulfonyl-phenyl)-N4-methyl-5-trifluoromethyl-pyrimidine-2,4-diamine | 0.017 |
| 17 | 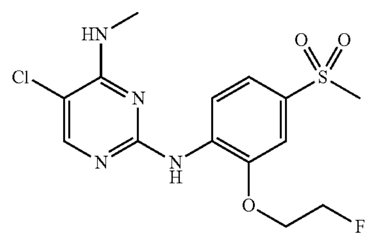 [SMILES: CNc1nc(Nc2ccc(S(C)(=O)=O)cc2OCCF)ncc1Cl] | 5-Chloro-N2-[2-(2-fluoro-ethoxy)-4-methanesulfonyl-phenyl]-N4-methyl-pyrimidine-2,4-diamine | 0.012 |
| 18 | 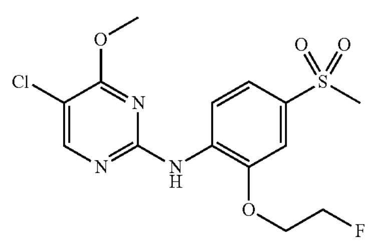 [SMILES: COc1nc(Nc2ccc(S(C)(=O)=O)cc2OCCF)ncc1Cl] | (5-Chloro-4-methoxy-pyrimidin-2-yl)-[2-(2-fluoro-ethoxy)-4-methanesulfonyl-phenyl]-amine | 0.012 |
| 19 | 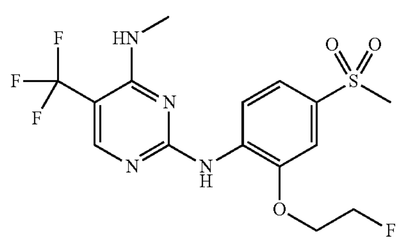 [SMILES: CNc1nc(Nc2ccc(S(C)(=O)=O)cc2OCCF)ncc1C(F)(F)F] | N2-[2-(2-Fluoro-ethoxy)-4-methanesulfonyl-phenyl]-N4-methyl-5-trifluoromethyl-pyrimidine-2,4-diamine | 0.003 |
| 20 | 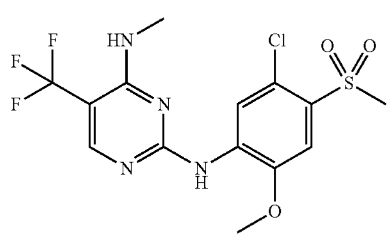 [SMILES: CNc1nc(Nc2cc(Cl)c(S(C)(=O)=O)cc2OC)ncc1C(F)(F)F] | N2-(5-Chloro-4-methanesulfonyl-2-methoxy-phenyl)-N4-methyl-5-trifluoromethyl-pyrimidine-2,4-diamine | 0.001 |

TABLE 3-continued

| | Structure | Name | K$_i$ |
|---|---|---|---|
| 21 | 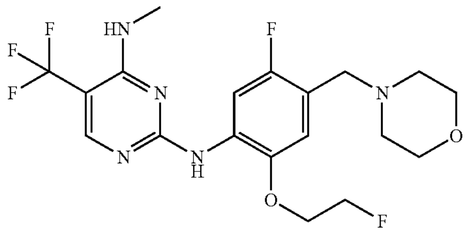 [SMILES: CNc1nc(Nc2cc(F)c(CN3CCOCC3)cc2OCCF)ncc1C(F)(F)F] | N2-[5-Fluoro-2-(2-fluoro-ethoxy)-4-morpholin-4-ylmethyl-phenyl]-N4-methyl-5-trifluoromethyl-pyrimidine-2,4-diamine | 0.004 |
| 22 | 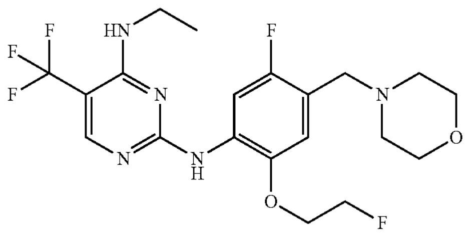 [SMILES: CCNc1nc(Nc2cc(F)c(CN3CCOCC3)cc2OCCF)ncc1C(F)(F)F] | N4-Ethyl-N2-[5-fluoro-2-(2-fluoro-ethoxy)-4-morpholin-4-ylmethyl-phenyl]-5-trifluoromethyl-pyrimidine-2,4-diamine | 0.002 |
| 23 | 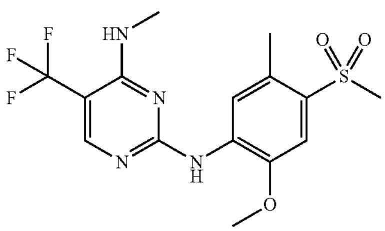 [SMILES: CNc1nc(Nc2cc(C)c(S(C)(=O)=O)cc2OC)ncc1C(F)(F)F] | N2-(4-Methanesulfonyl-2-methoxy-5-methyl-phenyl)-N4-methyl-5-trifluoromethyl-pyrimidine-2,4-diamine | 0.0003 |
| 24 | 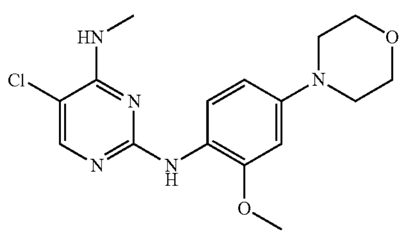 [SMILES: CNc1nc(Nc2ccc(N3CCOCC3)cc2OC)ncc1Cl] | 5-chloro-N2-(2-methoxy-4-morpholinophenyl)-N4-methylpyrimidine-2,4-diamine | 0.009 |
| 25 | 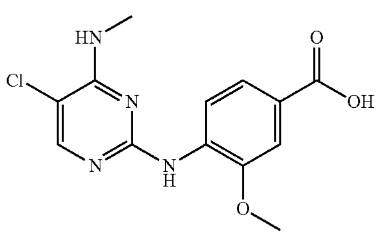 [SMILES: CNc1nc(Nc2ccc(C(=O)O)cc2OC)ncc1Cl] | 4-(5-chloro-4-(methylamino)pyrimidin-2-ylamino)-3-methoxybenzoic acid | 0.007 |
| 26 | 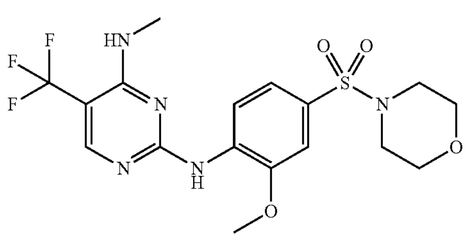 [SMILES: CNc1nc(Nc2ccc(S(=O)(=O)N3CCOCC3)cc2OC)ncc1C(F)(F)F] | N2-(2-methoxy-4-(morpholinosulfonyl)phenyl)-N4-methyl-5-(trifluoromethyl)pyrimidine-2,4-diamine | 0.047 |

TABLE 3-continued

| | Structure | Name | $K_i$ |
|---|---|---|---|
| 27 | 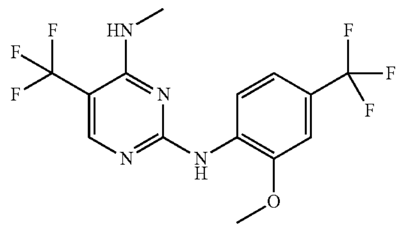 [SMILES: CNc1nc(Nc2ccc(C(F)(F)F)cc2OC)ncc1C(F)(F)F] | N2-(2-methoxy-4-(trifluoromethyl)phenyl)-N4-methyl-5-(trifluoromethyl)pyrimidine-2,4-diamine | 0.023 |
| 28 | 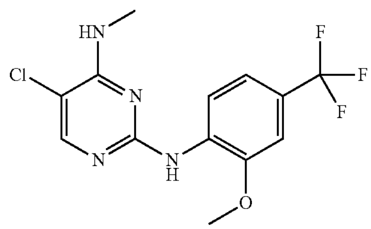 [SMILES: CNc1nc(Nc2ccc(C(F)(F)F)cc2OC)ncc1Cl] | 5-chloro-N2-(2-methoxy-4-(trifluoromethyl)phenyl)-N4-methylpyrimidine-2,4-diamine | 0.035 |
| 29 | 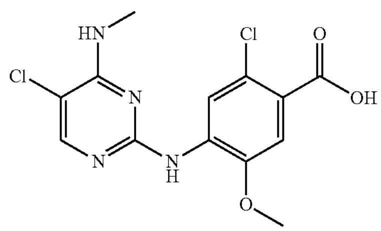 [SMILES: CNc1nc(Nc2cc(Cl)c(C(=O)O)cc2OC)ncc1Cl] | 2-chloro-4-(5-chloro-4-(methylamino)pyrimidin-2-ylamino)-5-methoxybenzoic acid | 0.036 |
| 30 | 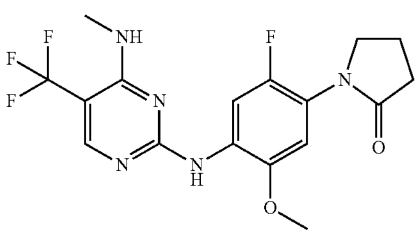 [SMILES: CNc1nc(Nc2cc(F)c(N3CCCC3=O)cc2OC)ncc1C(F)(F)F] | 1-(2-fluoro-5-methoxy-4-(4-(methylamino)-5-(trifluoromethyl)pyrimidin-2-ylamino)phenyl)pyrrolidin-2-one | 0.003 |
| 31 | 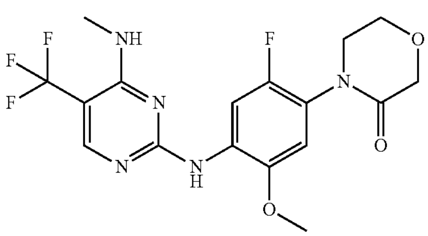 [SMILES: CNc1nc(Nc2cc(F)c(N3CCOCC3=O)cc2OC)ncc1C(F)(F)F] | 4-(2-fluoro-5-methoxy-4-(4-(methylamino)-5-(trifluoromethyl)pyrimidin-2-ylamino)phenyl)morpholin-3-one | 0.003 |
| 32 | 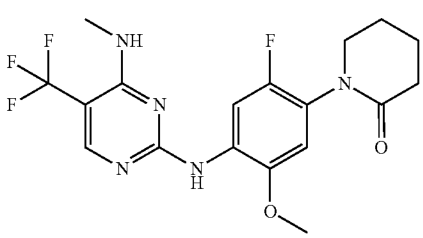 [SMILES: CNc1nc(Nc2cc(F)c(N3CCCCC3=O)cc2OC)ncc1C(F)(F)F] | 1-(2-fluoro-5-methoxy-4-(4-(methylamino)-5-(trifluoromethyl)pyrimidin-2-ylamino)phenyl)piperidin-2-one | 0.0055 |

TABLE 3-continued

| | Structure | Name | $K_i$ |
|---|---|---|---|
| 33 | 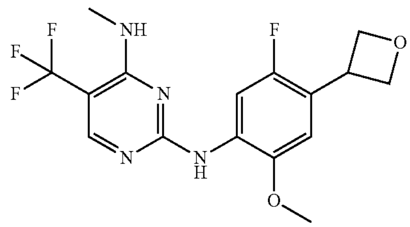 [SMILES: CNc1nc(Nc2cc(F)c(C3COC3)cc2OC)ncc1C(F)(F)F] | N2-(5-fluoro-2-methoxy-4-(oxetan-3-yl)phenyl)-N4-methyl-5-(trifluoromethyl)pyrimidine-2,4-diamine | 0.003 |
| 34 | 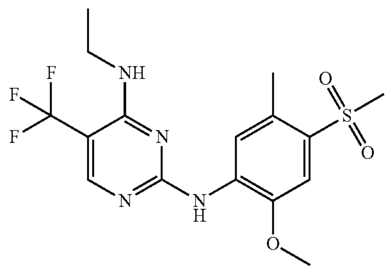 [SMILES: CCNc1nc(Nc2cc(C)c(S(C)(=O)=O)cc2OC)ncc1C(F)(F)F] | N4-ethyl-N2-(2-methoxy-5-methyl-4-(methylsulfonyl)phenyl)-5-(trifluoromethyl)pyrimidine-2,4-diamine | 0.003 |
| 35 | 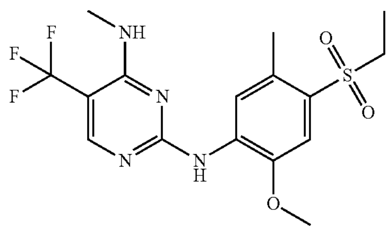 [SMILES: CCS(=O)(=O)c1cc(OC)c(Nc2ncc(C(F)(F)F)c(NC)n2)cc1C] | N2-(4-(ethylsulfonyl)-2-methoxy-5-methylphenyl)-N4-methyl-5-(trifluoromethyl)pyrimidine-2,4-diamine | 0.003 |
| 36 | 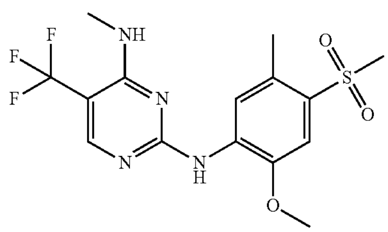 [SMILES: CNc1nc(Nc2cc(C)c(S(C)(=O)=O)cc2OC)ncc1C(F)(F)F] | N2-(2-methoxy-5-methyl-4-(methylsulfonyl)phenyl)-N4-methyl-5-(trifluoromethyl)pyrimidine-2,4-diamine | 0.003 |
| 37 | 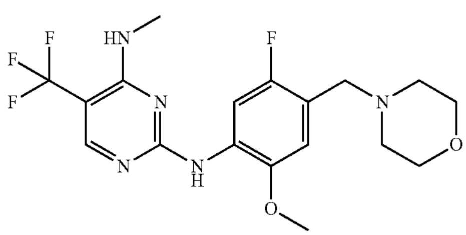 [SMILES: CNc1nc(Nc2cc(F)c(CN3CCOCC3)cc2OC)ncc1C(F)(F)F] | N2-(5-fluoro-2-methoxy-4-(morpholinomethyl)phenyl)-N4-methyl-5-(trifluoromethyl)pyrimidine-2,4-diamine | 0.056 |
| 38 | 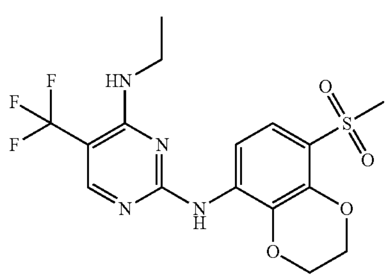 [SMILES: CCNc1nc(Nc2ccc(S(C)(=O)=O)c3c2OCCO3)ncc1C(F)(F)F] | N4-ethyl-N2-(8-(methylsulfonyl)-2,3-dihydrobenzo[b][1,4]dioxin-5-yl)-5-(trifluoromethyl)pyrimidine-2,4-diamine | 0.003 |

EXAMPLE 30

In Vitro LRRK2 LabChip Assay

This assay was used to determine a compound's potency in inhibiting activity of LRRK2 by determining, $Ki_{app}$, $IC_{50}$, or percent inhibition values. In a polypropylene plate, LRRK2, fluorescently-labeled peptide substrate, ATP and test compound were incubated together. Using a LabChip 3000 (Caliper Life Sciences), after the reaction the substrate was separated by capillary electrophoresis into two populations: phosphorylated and unphosphorylated. The relative amounts of each were quantitated by fluorescence intensity. LRRK2 Ki was determined according to the equation:

$$Y=V0*(1-((x+Ki*(1+S/Km)+Et)/(2*Et)-(((x+Ki*(1+S/Km)+Et)^2-(4*Et*x))^0.5)/(2*Et))).$$

Ki values in Table 4 and elsewhere herein are shown in µM.

Assay conditions and materials used were as follows:

Final Assay Conditions:
 LRRK2 G2019S in 5 mM $MgCl_2$: 5.2 nM (Invitrogen lot #567054A)
 LRRK2 G2019S in 1 mM $MnCl_2$: 11 nM (Invitrogen lot #567054A)
 LRRK2 Wild type in 5 mM $MgCl_2$: 15 nM (Invitrogen lot #500607F)
 LRRK2 I2020T in 5 mM $MgCl_2$: 25 nM (Invitrogen lot #43594)
 Substrate: 1 µM
 ATP: 130 µM
 Kinase reaction time: 2 hours
 Temperature: ambient
 Total volume: 20 µl $ATP^{app}$ Kms:
 G2019S in 5 mM $MgCl_2$: 130 µM
 G2019S in 1 mM $MnCl_2$: 1 µM
 Wild type in 5 mM $MgCl_2$: 80 µM
 I2020T in 5 mM $MgCl_2$: 14 µM Materials:
 Solid Support: Black 50 µL volume polypropylene 384 well plate (MatriCal cat #MP101-1-PP)
 Kinase: LRRK2 G2019S (Invitrogen cat #PV4882).
 LRRK2 Wild type (Invitrogen cat #PV4874).
 Substrate: 5FAM-GAGRLGRDKYKTLRQIRQ-$CONH_2$
 Non-binding plate: 384 well clear V-bottom polypropylene plates (Greiner cat #781280).
 ATP: 10 mM ATP (Cell Signaling cat #9804).
 Triton X-100: Triton X-100.
 Brij-35: Brij-35 (Pierce cat #20150).
 Coating Reagent #3: Coating Reagent #3 (Caliper).
 DMSO: DMSO (Sigma cat #34869-100ML).
 Complete Reaction Buffer: $H_2O$/25 mM Tris, pH 8.0/5 mM $MgCl_2$/2 mM DTT/0.01% Triton X-100.
 Stop Solution: $H_2O$/100 mM HEPES, pH 7.2/0.015% Brij-35/0.2% Coating Reagent #3/20 mM EDTA.
 Separation Buffer: $H_2O$/100 mM HEPES, pH 7.2/0.015% Brij-35/0.1% Coating Reagent #3/1:200 Coating Reagent #8/10 mM EDTA/5% DMSO.

Compound Plate Preparation:
 For serial dilutions, 34.6 µl DMSO was added to columns 3-24. For the assay controls, 37.5 µl DMSO was added to columns 1 and 2 of rows A and P. a,d and 50 µl 25 µM G-028831 (Staurosporine) was added to columns 1 and 2, row B. For the samples: to start at 100 µM, 37.5 µl DMSO was to columns 1 and 2, then 12.5 µl 10 mM compound; to start at 10 µM, 78 µl DMSO was added to columns 1 & 2, then 2 µl 10 mM compound; and to start at 1 µM, 25 µM compound (2 µl 10 mM cmpd+798 µl DMSO) was added to empty columns 1 and 2. A Precision instrument was used to perform 1:3.16 serial dilutions ("PLK_BM_serial_halflog").

ATP Preparation:
 ATP was diluted to 282.1 µM in Complete Kinase Buffer (final concentration was 130 µM).

Total and Blank Preparation:
 In Complete Reaction Buffer, substrate was diluted to 4 µM. Equal volumes of Complete Reaction Buffer and 4 µM substrate were combined to obtain the blank. Equal volumes of Complete Reaction Buffer and 4 µM substrate were combined and to the combined solution was added 2× final LRRK2 concentration.

Assay Procedure:
 To a 50 µl polypropylene plate, 5 µl/well buffer/substrate was added by hand to Blank wells. A Biomek FX was used to start the kinase reaction ("PLK SAR 23 ATP"). The following were added to the appropriate wells:
 2 µl compound+23 µl ATP;
 5 µl/well compound/ATP in Assay Plate;
 5 µl/well kinase/substrate in Assay Plate;
The plate was incubated for 2 hours in the dark. Biomek FX was used to stop the kinase reaction ("PLK Stop"), and 10 µl/well Stop solution was added to the Assay Plate. Results were read on the LabChip 3000.

Lab Chip 3000 Protocol:
 The LabChip 3000 was run using the job "LRRK2 IC50" with the following job settings:
 Pressure: −1.4 psi
 Downstream voltage: −500 V
 Upstream voltage: −2350 V
 Post sample buffer sip time: 75 seconds
 Post dye buffer sip time: 75 seconds
 Final delay time: 200 seconds

EXAMPLE 31

In Vitro LRRK2 Lanthascreen binding Assay

This assay was used to determine a compound's potency in inhibiting activity of LRRK2 by determining, $Ki_{app}$, $IC_{50}$, or percent inhibition values. In 384 well proxiplates F black, shallow well plates LRRK2, Eu-anti-GST-antibody, Alexa Fluor® Kinase tracer 236 and test compound were incubated together.

Binding of the Alexa Fluor® "tracer" to a kinase was detected by addition of a Eu-labeled anti-GST antibody. Binding of the tracer and antibody to a kinase results in a high degree of FRET, whereas displacement of the tracer with a kinase inhibitor results in a loss of FRET.

Assay conditions and materials used were as follows:

Final Assay Conditions:
 GST-LRRK2 G2019S 10 nM
 Eu-anti-GST-antibody 2 nM
 Kinase tracer 236 8.5 nM
 Kinase reaction time: 1 hour
 Temperature: ambient
 Total volume: 15 µl
 DMSO 1%

Materials:
 384 well proxiplates F black shallow well Perkin Elmer cat#6008260
 Kinase: LRRK2 G2019S Invitrogen cat #PV4882(LOT 567054A).
 Eu-labeled anti-GST antibody Invitrogen cat #PV5594
 Alexa Fluor® Kinase tracer 236 Invitrogen cat #PV5592
 TRIS-HCl Sigma cat #T3253

EGTA Sigma cat #E3889
Brij-35: Sigma cat #B4184(30% w/v)
DMSO: Sigma cat #D8418
MgCl$_2$ Sigma cat #M9272
Reaction Buffer: H$_2$O/50 mM Tris, pH 7.4/10 mM MgCl$_2$/1 mM EGTA/0.01% Brij 35.
Compound Plate Preparation:
Serially dilute test compounds (10 mM stock) 1:3.16 (20 ul+43.2 ul) in 100% DMSO. 12pt curve. Dilute each concentration 1:33.3 (3 ul+97 ul) in reaction buffer. Stamp 5 ul to assay plate. Final top test concentration 100 uM.
Total and Blank Preparation:
In Reaction Buffer, 5 ul of DMSO (3%) was added to total and blank wells and 5 ul of Eu-labeled anti-GST antibody(6 nM) was added to blank wells.
Assay Procedure:
Add 5 ul LRRK2(30 nM)/Eu-labeled anti-GST antibody (6 nM) mix to compound and total wells. Add 5 ul kinase tracer (25.5 nM) to all wells. Incubate plates at room temperature for 1 hour on a plate shaker (gentle shaking). Read on Perkin Elmer EnVision reader HTRF protocol.
Data Handling:
Calculate ratio: (665/620)*10000. Substract mean background values from all data points. Calculate % of control for each test value. Plot % of control vs Compound concentration. Calculate Ki Value (xlfit curve fitting—Morrison equation).
Results expressed as a Ki in μM. The equation for Ki:
Y=V0*(1−((x+Ki*(1+S/Km)+Et)/(2*Et)−(((x+Ki*(1+S/Km)+Et)^2−(4*Et*x))^0.5)/(2*Et)))
Where Et=4 nM
kd (Tracer)=8.5 nM
Tracer concentration (S)=8.5 nM.

EXAMPLE 32

Parkinson's Disease Animal Model

Parkinson's disease can be replicated in mice and in primates by administration of 1-methyl-4-phenyl tetrahydropyridine (MPTP), a selective nigrostriatal dopaminergic neurotoxin that produces a loss of striatal dopamine (DA) nerve terminal markers. Compounds of the invention may be evaluated for effectiveness in treatment of Parkinson's disease using MPTP induced neurodegeneration following generally the protocol described by Saporito et al., *J. Pharmacology* (1999) Vol. 288, pp. 421-427.
Briefly, MPTP is dissolved in PBS at concentrations of 2-4 mg/ml, and mice (male C57 weighing 20-25 g) are given a subcutaneous injection of 20 to 40 mg/kg. Compounds of the invention are solubilized with polyethylene glycol hydroxystearate and dissolved in PBS. Mice are administered 10 ml/kg of compound solution by subcutaneous injection 4 to 6 h before MPTP administration, and then daily for 7 days. On the day of the last injection, mice are sacrificed and the midbrain blocked and postfixed in paraformaldehyde. Striata are dissected free, weighed, and stored at −70° C.
The striata thus collected are evaluated for content of dopamine and its metabolites dihydroxyphenylacetic acid and homovanillic acid, by HPLC with electrochemical detection as described by Sonsalla et al., *J. Pharmacol. Exp. Ther.* (1987) Vol. 242, pp. 850-857. The striata may also be evaluated using the tyrosine hydroxylase assay of Okunu et al., *Anal Biochem* (1987) Vol. 129, pp. 405-411 by measuring $^{14}$CO$_2$ evolution associated with tyrosine hydroxylase-mediated conversion of labeled tyrosine to L-dopa. The striata may further be evaluated using the Monoamine oxidase-B assay as described by White et al., *Life Sci.* (1984), Vol. 35, pp. 827-833, and by monitoring dopamine uptake as described by Saporito et al., (1992) Vol. 260, pp. 1400-1409.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:
1. A compound of formula I:

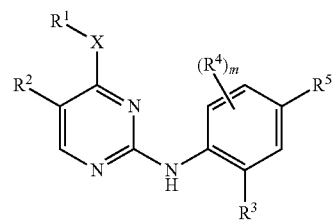

or a pharmaceutically acceptable salt thereof,
wherein:
  m is from 0 to 3;
  X is: —NR$^a$—; —O—; or —S(O)$_r$— wherein r is from 0 to 2 and R$^a$ is hydrogen or C$_{1-6}$alkyl;
  R$^1$ is: C$_{1-6}$alkyl;
  R$^2$ is: halo; C$_{1-6}$ alkoxy; cyano; halo-C$_{1-6}$ alkyl; halo-C$_{1-6}$ alkoxy; C$_{3-6}$cycloalkyl wherein the C$_{3-6}$cycloalkyl portion is optionally substituted with C$_{1-6}$alkyl; C$_{3-6}$cycloalkyl-C$_{1-6}$alkyl wherein the C$_{3-6}$cycloalkyl portion is optionally substituted with C$_{1-6}$alkyl; tetrahydrofuranyl; tetrahydrofuranyl-C$_{1-6}$alkyl; acetyl; oxetanyl; or oxetan-C$_{1-6}$ alkyl;
  R$^3$ and R$^4$ each independently is: halo; C$_{1-6}$alkyl; C$_{1-6}$alkoxy; C$_{3-6}$cycloalkyloxy; halo-C$_{1-6}$ alkyl; or halo-C$_{1-6}$alkoxy;
  or R$^3$ and R$^4$ together with the atoms to which they are attached may form a five-or six-membered ring that optionally includes one or two heteroatoms each independently selected from O, N and S, the ring being optionally substituted one or more times with R$^6$;
  R$^5$ is: C$_{1-6}$alkyl-sulfonyl; C$_{3-6}$cycloalkylsulfonyl; C$_{3-6}$cycloalkyl-C$_{1-6}$alkylsulfonyl; cyano; cyano-C$_{1-6}$alkyl; heterocyclyl optionally substituted one or more times with R$^6$; heterocyclyl-C$_{1-6}$alkyl wherein the heterocyclyl moiety is optionally substituted one or more times with R$^6$; halo-C$_{1-6}$alkyl; heterocyclyl-sulfonyl wherein the heterocyclyl moiety is optionally substituted one or more times with R$^6$; or carboxy; and
  R$^6$ is: C$_{1-6}$alkyl; halo; halo-C$_{1-6}$alkyl; or oxo.
2. The compound of claim 1, wherein m is 0 or 1.
3. The compound of claim 1, wherein X is —NH— or —O—.
4. The compound of claim 1, wherein R$^1$ is ethyl.
5. The compound of claim 1, wherein R$^1$ is methyl.
6. The compound of claim 1, wherein R$^2$ is: halo; halo-C$_{1-6}$ alkyl; or cyano.
7. The compound of claim 1, wherein R$^2$ is chloro or trifluoromethyl.

8. The compound of claim 1, wherein $R^3$ is fluoro, chloro or methoxy.

9. The compound of claim 1, wherein $R^3$ is methoxy.

10. The compound of claim 1, wherein $R^4$ is fluoro, chloro, methyl or methoxy.

11. The compound of claim 1, wherein $R^5$ is $C_{1-6}$alkylsulfonyl or cyano.

12. The compound of claim 1, wherein $R^5$ is $C_{1-6}$alkylsulfonyl.

13. The compound of claim 1, wherein $R^5$ is: methanesulfonyl; cyano; morpholin-4-yl-methyl; morpholin-4-yl; morpholin-4-yl-sulfonyl; or trifluoromethyl.

14. The compound of claim 1, wherein $R^5$ is: methanesulfonyl; cyano; or morpholin-4-yl-methyl.

15. The compound of claim 1, wherein $R^5$ is: methanesulfonyl; or cyano.

16. The compound of claim 1, wherein $R^5$ is cyano.

17. The compound of claim 1, wherein $R^5$ is methanesulfonyl.

18. A composition comprising:
    (a) a pharmaceutically acceptable carrier; and
    (b) a compound of claim 1.

19. A method for treating Parkinson's disease, said method comprising administering to a subject in need thereof an effective amount of a compound of claim 1.

20. The compound of claim 1, wherein said compound is selected from:
   N2-(2-Methoxy-4-(methylsulfonyl)phenyl)-N4-methyl-5-(trifluoromethyl)pyrimidine-2,4-diamine;
   5-Chloro-N2-(2-methoxy-4-(methylsulfonyl)phenyl)-N4-methylpyrimidine-2,4-diamine;
   2-Fluoro-5-methoxy-4-(4-(methylamino)-5-(trifluoromethyl)pyrimidin-2-ylamino)benzonitrile;
   3-Methoxy-4-(4-(methylamino)-5-(trifluoromethyl)pyrimidin-2-ylamino)benzonitrile;
   4-(5-Chloro-4-(methylamino)pyrimidin-2-ylamino)-3-methoxybenzonitrile;
   (2-Chloro-4-methanesulfonyl-phenyl)-(5-chloro-4-methoxy-pyrimidin-2-yl)-amine;
   N2-(2-Chloro-4-methanesulfonyl-phenyl)-N4-methyl-5-trifluoromethyl-pyrimidine-2,4-diamine;
   5-Chloro-N2-(2-chloro-4-methanesulfonyl-phenyl)-N4-methyl-pyrimidine-2,4-diamine;
   N2-(2-Methoxy-4-morpholin-4-ylmethyl-phenyl)-N4-methyl-5-trifluoromethyl-pyrimidine-2,4-diamine;
   5-Chloro-2-methyl-4-(4-methylamino-5-trifluoromethyl-pyrimidin-2-ylamino)-benzonitrile;
   2-(5-Fluoro-2-methoxy-4-morpholin-4-ylmethyl-phenylamino)-4-methylamino-pyrimidine-5-carbonitrile;
   4-Ethylamino-2-(5-fluoro-2-methoxy-4-morpholin-4-ylmethyl-phenylamino)-pyrimidine-5-carbonitrile;
   5 -Methoxy-2-methyl-4-(4-methylamino-5 -trifluoromethyl-pyrimidin-2-ylamino)-benzonitrile;
   5-Chloro-N2[2-(2-fluoro-ethoxy)-4-morpholin-4-ylmethyl-phenyl]-N4-methyl-pyrimidine-2,4-diamine;
   N2-(5-Fluoro-4-methanesulfonyl-2-methoxy-phenyl)-N4-methyl-5-trifluoromethyl-pyrimidine-2,4-diamine;
   N2-(2-Isopropoxy-4-methanesulfonyl-phenyl)-N4-methyl-5 -trifluoromethyl-pyrimidine-2,4-diamine;
   5-Chloro-N2-[2-(2-fluoro-ethoxy)-4-methanesulfonyl-phenyl]-N4-methyl-pyrimidine-2,4-diamine;
   (5-Chloro-4-methoxy-pyrimidin-2-yl)-[2-(2-fluoro-ethoxy)-4-methanesulfonyl-phenyl]-amine;
   N2[2-(2-Fluoro-ethoxy)-4-methanesulfonyl-phenyl]-N4-methyl-5-trifluoromethyl-pyrimidine-2,4-diamine;
   N2-(5-Chloro-4-methanesulfonyl-2-methoxy-phenyl)-N4-methyl-5-trifluoromethyl-pyrimidine-2,4-diamine;
   N2[5-Fluoro-2-(2-fluoro-ethoxy)-4-morpholin-4-ylmethyl-phenyl]-N4-methyl-5-trifluoromethyl-pyrimidine-2,4-diamine;
   N4-Ethyl-N2-[5-fluoro-2-(2-fluoro-ethoxy)-4-morpholin-4-ylmethyl-phenyl]-5-trifluoromethyl-pyrimidine-2,4-diamine;
   N2-(4-Methanesulfonyl-2-methoxy-5-methyl-phenyl)-N4-methyl-5-trifluoromethyl-pyrimidine-2,4-diamine;
   5-chloro-N2-(2-methoxy-4-morpholinophenyl)-N4-methylpyrimidine-2,4-diamine;
   4-(5-chloro-4-(methylamino)pyrimidin-2-ylamino)-3-methoxybenzoic acid;
   N2-(2-methoxy-4-(morpholinosulfonyl)phenyl)-N4-methyl-5-(trifluoromethyl)pyrimidine-2,4-diamine;
   N2-(2-methoxy-4-(trifluoromethyl)phenyl)-N4-methyl-5-(trifluoromethyl)pyrimidine-2,4-diamine;
   5-chloro-N2-(2-methoxy-4-(trifluoromethyl)phenyl)-N4-methylpyrimidine-2,4-diamine;
   2-chloro-4-(5-chloro-4-(methylamino)pyrimidin-2-ylamino)-5-methoxybenzoic acid;
   1-(2-fluoro-5-methoxy-4-(4-(methylamino)-5-(trifluoromethyl)pyrimidin-2-ylamino)phenyl)pyrrolidin-2-one;
   4-(2-fluoro-5-methoxy-4-(4-(methylamino)-5-(trifluoromethyl)pyrimidin-2-ylamino)phenyl)morpholin-3-one;
   1-(2-fluoro-5-methoxy-4-(4-(methylamino)-5-(trifluoromethyl)pyrimidin-2-ylamino)phenyl)piperidin-2-one;
   N2-(5-fluoro-2-methoxy-4-(oxetan-3-yl)phenyl)-N4-methyl-5-(trifluoromethyl)pyrimidine-2,4-diamine;
   N4-ethyl-N2-(2-methoxy-5-methyl-4-(methylsulfonyl)phenyl)-5-(trifluoromethyl)pyrimidine-2,4-diamine;
   N2-(4-(ethylsulfonyl)-2-methoxy-5 -methylphenyl)-N4-methyl-5 -(trifluoromethyl)pyrimidine-2,4-diamine;
   N2-(2-methoxy-5-methyl-4-(methylsulfonyl)phenyl)-N4-methyl-5-(trifluoromethyl)pyrimidine-2,4-diamine;
   N2-(5-fluoro-2-methoxy-4-(morpholinomethyl)phenyl)-N4-methyl-5-(trifluoromethyl)pyrimidine-2,4-diamine; and
   N4-ethyl-N2-(8-(methylsulfonyl)-2,3-dihydrobenzo[b][1,4]dioxin-5-yl)-5-(trifluoromethyl)pyrimidine-2,4-diamine.

* * * * *